(12) United States Patent
Shirai et al.

(10) Patent No.: US 12,159,414 B2
(45) Date of Patent: Dec. 3, 2024

(54) HEAT TRACE AREA EXTRACTION APPARATUS, HEAT TRACE AREA EXTRACTION METHOD AND PROGRAM

(71) Applicant: NIPPON TELEGRAPH AND TELEPHONE CORPORATION, Tokyo (JP)

(72) Inventors: Yoshinari Shirai, Tokyo (JP); Yasue Kishino, Tokyo (JP); Shin Mizutani, Tokyo (JP); Kazuya Ohara, Tokyo (JP); Takayuki Suyama, Tokyo (JP)

(73) Assignee: NIPPON TELEGRAPH AND TELEPHONE CORPORATION, Tokyo (JP)

( * ) Notice: Subject to any disclaimer, the term of this patent is extended or adjusted under 35 U.S.C. 154(b) by 42 days.

(21) Appl. No.: 18/031,141

(22) PCT Filed: Oct. 12, 2021

(86) PCT No.: PCT/JP2021/037676
§ 371 (c)(1),
(2) Date: Apr. 10, 2023

(87) PCT Pub. No.: WO2022/080350
PCT Pub. Date: Apr. 21, 2022

(65) Prior Publication Data
US 2023/0384162 A1    Nov. 30, 2023

(30) Foreign Application Priority Data
Oct. 16, 2020   (WO) .................. PCT/JP2020/039126

(51) Int. Cl.
*G06T 7/11* (2017.01)
*G01J 5/00* (2022.01)
(Continued)

(52) U.S. Cl.
CPC ............... *G06T 7/11* (2017.01); *G01J 5/0025* (2013.01); *G01J 5/0859* (2013.01); *G01J 5/48* (2013.01);
(Continued)

(58) Field of Classification Search
None
See application file for complete search history.

(56) References Cited

U.S. PATENT DOCUMENTS

2017/0091944 A1*  3/2017  Taguchi ................. H04N 23/90

OTHER PUBLICATIONS

TECHABLE (2020) "Efficient disinfection of stadiums using drones! US startup invented with new corona" literature [online] Accessed on May 18, 2020, website: https://techable.jp/archives/124749.
(Continued)

*Primary Examiner* — Christopher Braniff

(57) ABSTRACT

A heat trace region extraction device includes: a difference actual object image generation unit 130 that generates a difference actual object image which is an image of a difference between an actual object image which is an image of an actual object obtained by photographing a certain range with an actual object camera for photographing the actual object and a background actual object image which is an actual object image of a background of the certain range; a difference thermal image generation unit 16 that generates a difference thermal image which is an image of a difference between a thermal image which is an image of heat emitted by the actual object obtained by photographing the certain range with a thermal camera for photographing the heat emitted by the actual object and a background thermal image which is a thermal image of the background; and a heat trace region extraction unit 17 that extracts a heat trace region by removing a region of the actual object from the thermal image based on the difference actual object image and the difference thermal image.

20 Claims, 22 Drawing Sheets

(51) Int. Cl.
 G01J 5/08 (2022.01)
 G01J 5/48 (2022.01)
 G06T 7/174 (2017.01)
 G06T 7/194 (2017.01)
 G16H 30/40 (2018.01)
 G16H 50/80 (2018.01)
 H04N 7/18 (2006.01)
 H04N 23/20 (2023.01)

(52) U.S. Cl.
 CPC .............. *G06T 7/174* (2017.01); *G06T 7/194* (2017.01); *G16H 30/40* (2018.01); *G16H 50/80* (2018.01); *H04N 7/18* (2013.01); *H04N 23/20* (2023.01); *G01J 2005/0077* (2013.01); *G06T 2207/10048* (2013.01); *G06T 2207/20224* (2013.01); *G06T 2207/30196* (2013.01)

(56) References Cited

OTHER PUBLICATIONS

Yoshida et al. (2011) "Contact detection using image recognition" 2011 Kyushu Section Joint Conference of Institutes of Electrical and Related Engineers, Sep. 26, 2011.
Kishino et al. (2020) "Identifying Human Contact Points on Environmental Surfaces using Heat Traces to Support Disinfect Activities: poster abstract" Proceedings of the 18th Conference on Embedded Networked Sensor Systems, Nov. 16, 2020, pp. 768-769 [online] website: https://dl.acm.org/doi/10.1145/3384419.3430597.
Shirai et al. (2020) "Alertable Surfaces: A real-world environment that can warn of virus attachment" 28th Workshop on Interactive Systems and Software (WISS2020), Dec. 17, 2020.
Shirai et al. (2021) "Series—Teacher, I have a question!" Information Processing vol. 62, No. 5, pp. 264-265.
Nippon Telegraph and Telephone Corporation (2021) "A function that visualizes the places touched by people can be easily realized in a real environment—I want to know about the corona wreck: Where did everyone touch?" NTT Holding Company News Release, May 31, 2021 [online] website: https://group.ntt/jp/newsrelease/2021/05/31/210531a.html.
Yasue Kishino (2021) "I want to know about the corona disaster: where did everyone touch?—Touched places detection using heat traces by thermography" NTT Communication Science Laboratories Open House 2021, Research Exhibit 18, Jun. 3, 2021 [online] website: http://www.kecl.ntt.co.jp/openhouse/2021/exhibition_18.html.
Yasue Kishino (2021) "Visualization method of touched places to prevent new corona virus infection" Intelligent Sensing and Interaction Symposium 2021 (ISIS 2021), Jun. 8, 2021.
Yasue Kishino (2021) "Visualize the places touched by people and project them in an easy-to-understand manner to reduce anxiety about the corona disaster" Business Communication, vol. 58, No. 8, pp. 16-19.

\* cited by examiner

Fig. 15

| TIME | FILE NAME | GROUP ID |
|---|---|---|
| 2021-08-10 10:10:40.000 | 000925.bmp | 25 |
| 2021-08-10 10:10:40.500 | 000926.bmp | 25 |
| 2021-08-10 10:10:41.000 | 000927.bmp | 25 |
| ... | ... | ... |
| 2021-08-10 10:50:40.000 | 001005.bmp | 27 |
| 2021-08-10 10:50:40.500 | 001006.bmp | 27 |
| 2021-08-10 10:50:41.000 | 001007.bmp | 27 |
| 2021-08-10 10:50:48.000 | 001020.bmp | |

Fig. 19

| GROUP ID | TEMPERATURE | EXPRESSION |
|---|---|---|
| 25 | 36.2 | 1 |
| 26 | 36.6 | 1 |
| 27 | 38.7 | 9 |
| 28 | 37.5 | 6 |
| | | |
| | | |
| | | |
| | | |
| | | |
| | | |

HEAT TRACE AREA EXTRACTION APPARATUS, HEAT TRACE AREA EXTRACTION METHOD AND PROGRAM

CROSS-REFERENCE TO RELATED APPLICATIONS

This application is a U.S. National Stage Application filed under 35 U.S.C. § 371 claiming priority to International Patent Application No. PCT/JP2021/037676, filed on 12 Oct. 2021, which application claims priority to and the benefit of International Patent Application No. PCT/JP2020/039126, filed on 16 Oct. 2020, the disclosures of which are hereby incorporated herein by reference in their entireties.

TECHNICAL FIELD

The present invention relates to a heat trace region extraction device, a heat trace region extraction method and a program.

BACKGROUND ART

With the epidemic of the new coronavirus infection (COVID-19), various measures have been taken to prevent infection, one of which is disinfection or sterilization. If the mucous membrane of the mouth, nose, or eyes is touched with a finger to which this virus is attached, there will be infection with the virus. Therefore, it is recommended to disinfect not only the fingers but also personal items that an infected person may have touched. Therefore, in restaurants and sports gyms used by many people, measures are taken such as regularly wiping desks, doors, training equipment, and the like with alcohol disinfectant or the like.

It is difficult to continue visually checking which portions have actually been touched. In stores, measures such as disinfecting all places that may have been touched by people are often taken at regular intervals. However, the task of disinfecting all places that may have been touched by people on a regular basis involves a large amount of labor.

Therefore, a method for improving the efficiency of disinfection using a drone has been proposed (for example, NPL 1).

On the other hand, it is also conceivable to use a surveillance camera or the like to detect the place where persons are present and disinfect only that place. There has been much research on human detection using video, and in recent years it has become possible to identify the place where a person is present from a video with considerably high accuracy. If it is possible to disinfect only the place where a person was present using such a technique, it is considered that the labor for disinfection can be reduced. For example, it is not necessary to disinfect the region around a place when it has not been used by people at all. On the other hand, if it is known that a plurality of persons have used a place, it should be possible to disinfect the place at an early stage. Disinfection at regular time intervals cannot prevent infections mediated by objects, that is, infections caused by an infected person touching an object and another person touching the object within an interval. However, if there can be disinfection flexibly according to human use, it is thought that such spread of infection can be further reduced. In addition, since such a method can prevent unnecessary disinfection, the effect of reducing the amount of disinfectant solution used can be expected. In other words, if disinfection can be performed according to the use of objects by a person detected by surveillance cameras, labor will be reduced, the spread of infection can be prevented, and disinfectant solution can be saved as compared with the case of disinfecting all objects that may have been used at regular time intervals.

If it is possible to disinfect only the places that people actually touched in a pinpoint manner, instead of disinfecting everything around the place where people were, it would be possible to further reduce labor and disinfectant solution. However, it is difficult to identify whether a person who was actually at a place touched an object by the method using a visible video captured by a surveillance camera or the like. For example, supposing that a camera is installed downward from the ceiling and a table is being imaged, when a hand is extended onto the table, it may be difficult to determine whether the hand is touching the desk from the video taken by the installed camera. Therefore, a method for detecting contact with an object using a shadow has been proposed (NPL 2).

CITATION LIST

Non Patent Literature

[NPL 1] "Efficiently disinfecting a stadium with a drone! Invented by US startup with the new Corona," [online], Internet, <URL:https://techable.jp/archives/124749>

[NPL 2] Tatsuo Yoshida, Hon Yaokai, Seiichi Uchida, Contact detection using image recognition, Electrical Society, Kyushu Branch Joint Conference 2011.

SUMMARY OF INVENTION

Technical Problem

However, the method of NPL 2 requires a strong light source such as a projector. In addition, it is assumed that the recognition accuracy is significantly affected by the positional relationship between the camera and the light source. A strong light source cannot be installed freely in many environments, and it is considered that it is not suitable for the purpose of detecting and presenting a place touched by a person in various places to support disinfection.

The present invention has been made in view of the above-mentioned problems, and an object thereof is to improve the detection accuracy of the place touched by a person.

Solution to Problem

In order to solve the above problem, a heat trace region extraction device includes: a difference actual object image generation unit that generates a difference actual object image which is an image of a difference between an actual object image which is an image of an actual object obtained by photographing a certain range with an actual object camera for photographing the actual object and a background actual object image which is an actual object image of a background of the certain range; a difference thermal image generation unit that generates a difference thermal image which is an image of a difference between a thermal image which is an image of heat emitted by the actual object obtained by photographing the certain range with a thermal camera for photographing the heat emitted by the actual object and a background thermal image which is a thermal image of the background; and a heat trace region extraction unit that extracts a heat trace region by removing a region of the actual object from the thermal image based on the difference actual object image and the difference thermal image.

Advantageous Effects of Invention

According to the present invention, it is possible to improve the detection accuracy of the place touched by a person.

BRIEF DESCRIPTION OF DRAWINGS

FIG. 15 is a diagram for explaining the third embodiment.
FIG. 19 is a diagram for explaining the third embodiment.

DESCRIPTION OF EMBODIMENTS

Overview

Figure 1:
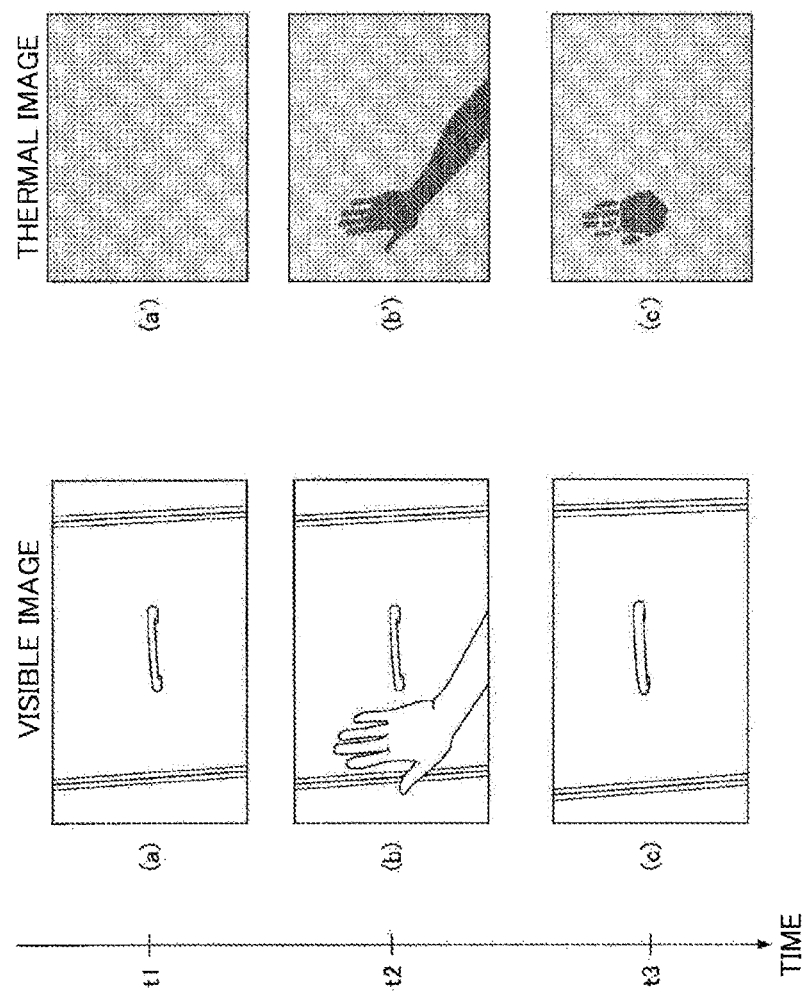
FIG. 1 is a schematic diagram of a visible image and a thermal image of the same place taken at the same time.

In the first embodiment, a device, a method, and a program for detecting a place touched by a person using a thermal image are disclosed with the aim to help sterilize or disinfect bacteria or viruses. Since a person who is a homeothermic animal has heat on his/her limbs, when the person touches an object, the heat remains in the place touched by the person for a certain period of time. For example, a method of abusing the heat trace, which is a trace of human touch identified by the heat remaining in the place touched by the person, to decrypt the passcode of a smartphone has been reported ("Yomna Abdelrahman, Mohamed Khamis, Stefan Schneegass, and Florian Alt. 2017. Stay Cool! Understanding Thermal Attacks on Mobile-based User Authentication. In Proceedings of the 2017 CHI Conference on Human Factors in Computing Systems (CHI '17), pp. 3751.3763, 2017").

Heat traces remain not only on the screens of smartphones, but also on various places such as desks and walls. Therefore, if the heat trace is identified based on the video (thermal image) of a thermal camera, the place touched by a person indoors or the like can be pinpointed. A thermal image is an image (that is, an image obtained by photographing rays of heat radiated by an actual object) of heat emitted by an actual object, obtained by photographing a certain range with a thermal camera for photographing the heat emitted by the actual object (that is, the rays of heat radiated by the actual object and the electromagnetic waves having the wavelength in the far-infrared region). More specifically, the thermal image is an image of a temperature distribution by detecting the infrared radiation energy emitted from an object and converting it into an apparent temperature. In other words, a thermal image is not an image of the infrared rays reflected by the actual object.

The heat trace region can be extracted by background subtraction with the thermal image before being touched by a person as the background. However, since the human body itself is hot, this method extracts the human body region as well as the heat trace. Therefore, in the first embodiment, a visible image is acquired at the same time as the thermal image, and the heat trace region is extracted by comparing the thermal image with the visible image.

Specifically, background subtraction is performed for each of the visible image and the thermal image, and the heat trace region is extracted by the difference in the result of the background subtraction. Since heat traces cannot be observed with a visible image (that is, with the naked eye), they cannot be extracted even if background subtraction is performed on the visible image with the visible image before being touched by a person as the background. On the other hand, when there is a person on the spot, the region of the person is extracted by performing background subtraction with the visible image taken in the absence of the person as the background. That is, when the region extracted by background subtraction in the thermal image is similarly extracted in the visible image, it can be seen that the region is not a heat trace. On the other hand, the region extracted in the thermal image by background subtraction and not extracted in the visible image is likely to be a heat trace. In the first embodiment, the heat trace region extracted by such a method is visualized, and the place touched by a person is transmitted to the user. For simultaneous acquisition of thermal and visible images, a device such as a sensor node equipped with a visible light camera and a thermal camera may be used ("Yoshinari Shirai, Yasue Kishino, Takayuki Suyama, Shin Mizutani: PASNIC: a thermal based privacy-aware sensor node for image capturing, UbiComp/ISWC '19 Adjunct, pp. 202-205, 2019").

First Embodiment

The object of the first embodiment will be described with reference to FIGS. 1 and 2. FIG. 1 is a schematic diagram of a visible image and a thermal image of the same place taken at the same place. FIG. 1 shows a schematic diagram of an image of a hand touching a door with a handle taken simultaneously with a visible light camera and a thermal camera. FIG. 1(a) and FIG. 1(a') are a visible image and a thermal image at time t1 (before the hand touches the door), respectively. FIG. 1(b) and FIG. 1(b') are a visible image and a thermal image at time t2 (a state in which the hand is touching the door), respectively. FIG. 1(c) and FIG. 1(c') are a visible image and a thermal image at time t3 (after the hand touches the door). When a person touches the door, the temperature of the touched place rises as shown in FIG. 1(c').

Figure 2:
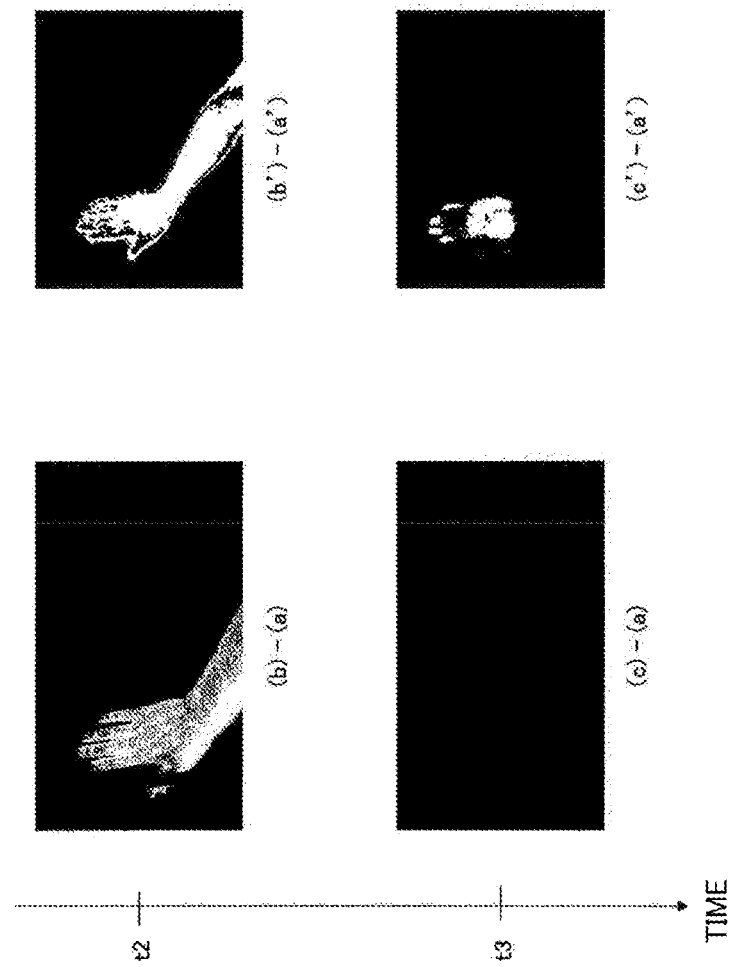
FIG. 2 is a diagram showing an example of an image obtained by background subtraction.

FIG. 2 is a diagram showing an example of an image obtained by background subtraction. FIG. 2 shows a difference image which is the background subtraction between the image at time t2 and the image at time t3 when the image at time t1 in FIG. 1 is used as the background image. At time t2, the arm portion is extracted as a difference region where there is a difference from the background image in both the visible image and the thermal image. In contrast, at time t3, the portion touching the door is extracted as a difference region only in the thermal image.

Considering disinfecting the region actually touched by the hand, the difference region extracted by background subtraction with respect to the thermal image (background thermal image) at time t1 of the thermal image at time t3 may be disinfected. On the other hand, the difference region extracted by background subtraction with respect to the thermal image (background thermal image) at time t1 of the thermal image at time t2 includes a portion not touching the door. In the first place, the difference region extracted by the background subtraction of the thermal image at time t2 with respect to the thermal image (background thermal image) at time t1 is the region where the human body existed, and is not the region of heat trace left by actually touching the door. From the viewpoint of disinfection, it is sufficient to identify the difference region extracted by the background subtraction at time t3, and the difference region extracted by the background subtraction at time t2 is unnecessary.

Therefore, in the first embodiment, when a similar difference region is extracted by background subtraction even in a visible image, it is determined that the difference region is not a heat trace region. At time t2, since the shape of the arm is also extracted in the visible image, it is determined that the difference region extracted in the thermal image is not a heat trace region (that is, a portion touched by a person). On the other hand, at time t3, it is determined that the region extracted by the background subtraction of the thermal image is not extracted in the visible image, so that the difference region extracted in the thermal image is the heat trace region (that is, the portion touched by a person). If a system presents information indicating the heat trace region extracted based on such a determination, the user who sees the information can efficiently disinfect the portion touched by a person.

Figure 3:
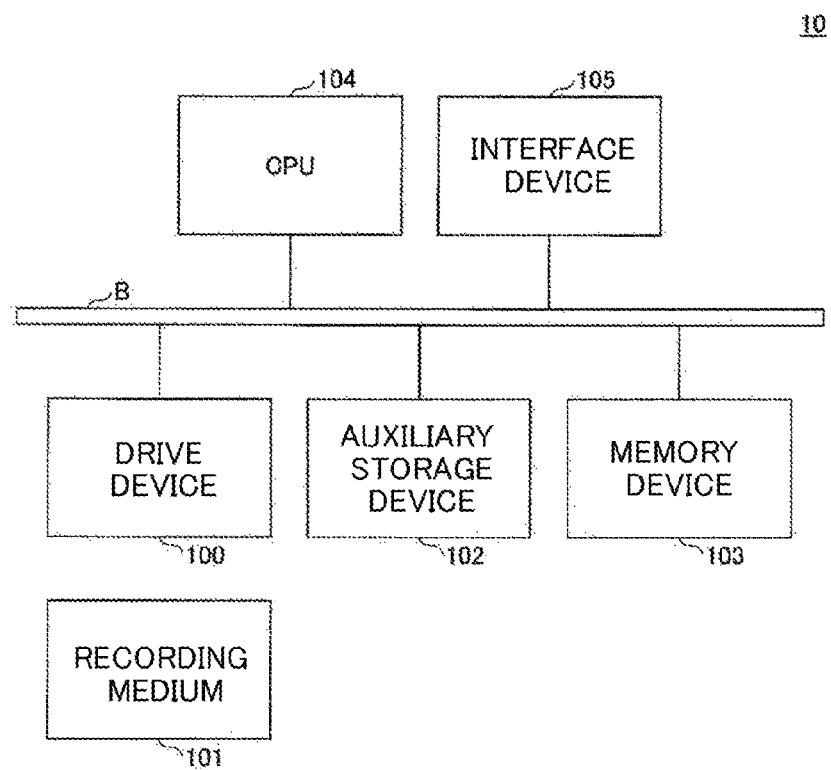
FIG. 3 is a diagram showing a hardware configuration example of a heat trace region extraction device 10 according to the first to fifth embodiments.

Hereinafter, the heat trace region extraction device 10 that realizes the above will be specifically described. FIG. 3 is a diagram showing a hardware configuration example of the heat trace region extraction device 10 in the first embodiment, a modified example described later of the first embodiment, and the second to fifth embodiments. The heat trace region extraction device 10 of FIG. 3 has a drive device 100, an auxiliary storage device 102, a memory device 103, a CPU 104, an interface device 105, and the like, which are connected to each other by a bus B.

The program that realizes the processing in the heat trace region extraction device 10 is provided by a recording medium 101 such as a CD-ROM. When the recording medium 101 storing the program is set in the drive device 100, the program is installed in the auxiliary storage device 102 from the recording medium 101 via the drive device 100. However, the program does not necessarily have to be installed from the recording medium 101, and may be downloaded from another computer via the network. The auxiliary storage device 102 stores the installed program and also stores necessary files, data, and the like.

The memory device 103 reads and stores the program from the auxiliary storage device 102 when an instruction for starting the program is issued. The CPU 104 executes the function related to the heat trace region extraction device 10 according to the program stored in the memory device 103. The interface device 105 is used as an interface for connecting to a network.

Figure 4:
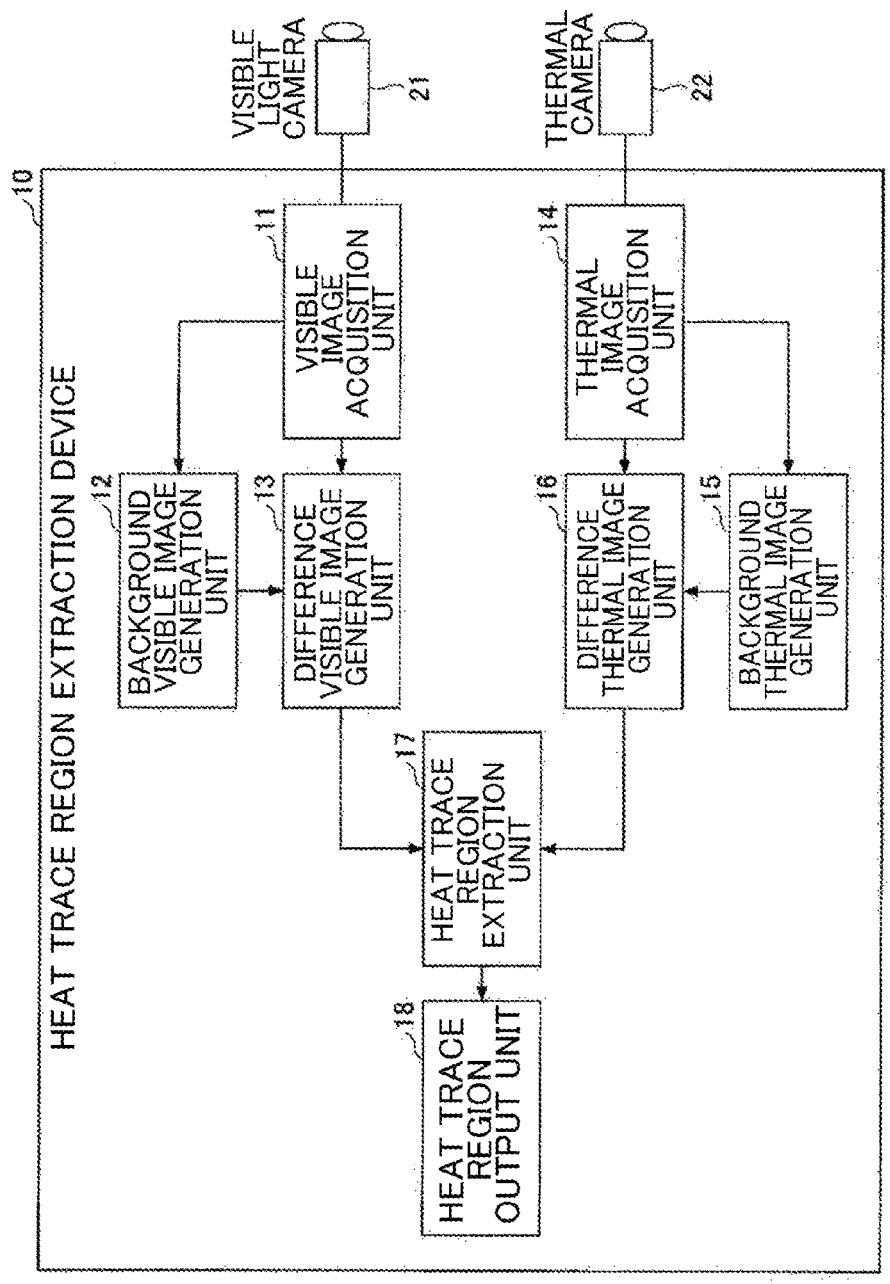
FIG. 4 is a diagram showing a functional configuration example of the heat trace region extraction device 10 in the first embodiment.

FIG. 4 is a diagram showing a functional configuration example of the heat trace region extraction device 10 in the first embodiment. In FIG. 4, the heat trace region extraction device 10 includes a visible image acquisition unit 11, a background visible image generation unit 12, a difference visible image generation unit 13, a thermal image acquisition unit 14, a background thermal image generation unit 15, a difference thermal image generation unit 16, a heat trace region extraction unit 17, a heat trace region output unit 18, and the like. Each of these units is realized by one or more programs installed in the heat trace region extraction device causing the CPU 104 to execute processing.

As shown in FIG. 4, the heat trace region extraction device 10 is connected to each of a visible light camera 21 and a thermal camera 22 so that images can be input from the cameras. The visible light camera 21 and the thermal camera 22 are installed so as to be able to photograph the same certain place (the same certain range). That is, the first embodiment is based on the assumption that the photographing region of the visible light camera 21 and the photographing region of the thermal camera 22 match each other on a pixel-by-pixel basis. If the photographed portions of the visible light camera 21 and the thermal camera 22 do not match, calibration may be performed in advance so that the correspondence between the pixels of the visible image and the thermal image can be grasped.

Figure 5:
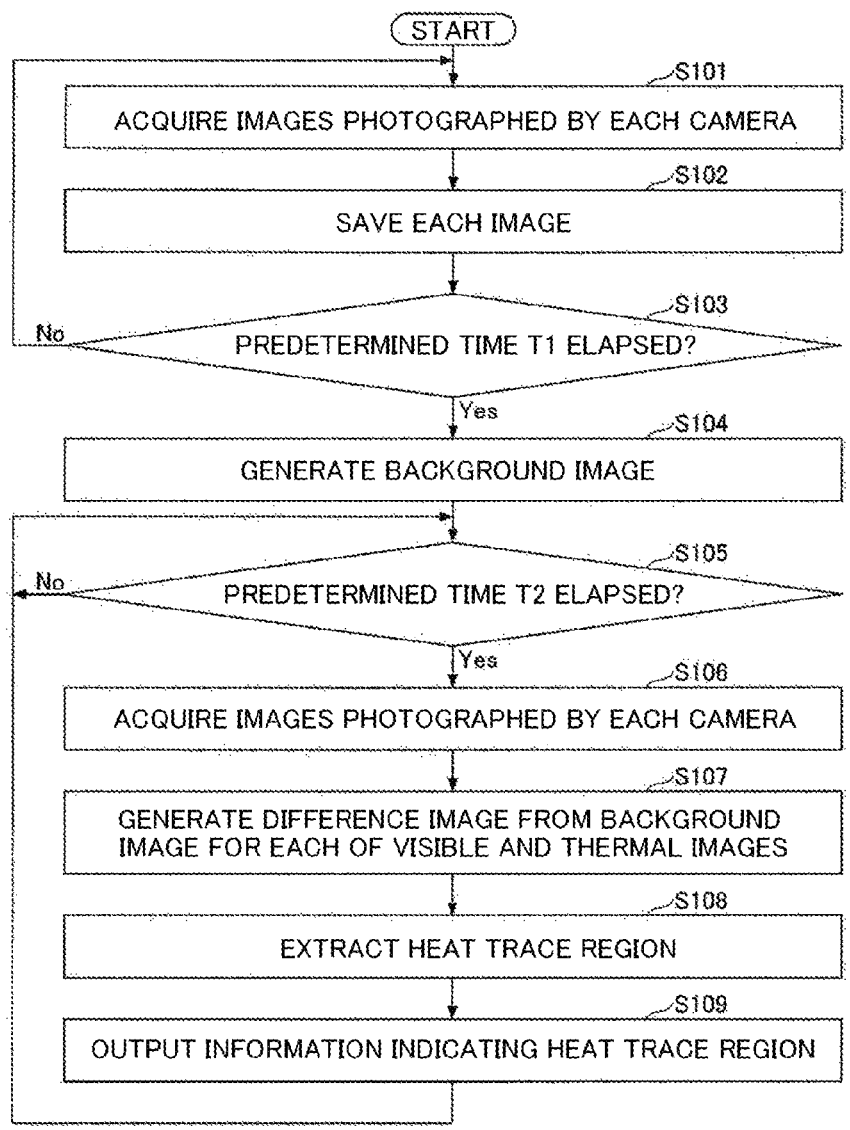
FIG. 5 is a flowchart for explaining an example of a processing procedure executed by the heat trace region extraction device 10 in the first embodiment.

FIG. 5 is a flowchart for explaining an example of a processing procedure executed by the heat trace region extraction device 10.

In step S101, the visible image acquisition unit 11 acquires the visible image photographed by the visible light camera 21, input from the visible light camera 21, and the thermal image acquisition unit 14 acquires the thermal image photographed by the thermal camera 22, input from the thermal camera 22. In step S101, the acquisition of the visible image by the visible image acquisition unit 11 and the acquisition of the thermal image by the thermal image acquisition unit 14 may or may not be performed at the same time. If not at the same time, a portion of the frame of the camera with the faster frame rate may be ignored according to the camera with the slower frame rate. Further, there is no problem even if still images are alternately acquired from the visible light camera 21 and the thermal camera 22 and the acquired images are regarded as being acquired at the same time as long as the frame rate is high to some extent. The visible image acquisition unit 11 transmits the acquired visible image to the background visible image generation unit 12, and the thermal image acquisition unit 14 transmits the acquired thermal image to the background thermal image generation unit 15.

Subsequently, the background visible image generation unit 12 stores the visible image transmitted from the visible image acquisition unit 11 in the auxiliary storage device 102, and the background thermal image generation unit 15 stores the thermal image transmitted from the thermal image acquisition unit 14 in the auxiliary storage device 102 (S102).

Steps S101 and S102 are repeated until a predetermined time T1 elapses from the start of execution. The predetermined time T1 may be a period in which one or more visible images and one or more thermal images are accumulated in the auxiliary storage device 102.

When the predetermined time T1 has elapsed from the start of execution of the first step S101 (Yes in S103), the processing proceeds to step S104. In step S104, the background visible image generation unit 12 generates a background image (hereinafter, referred to as "background visible image") in the photographing range based on the visible image group stored in the auxiliary storage device 102 at the predetermined time T1. In step S104, the background thermal image generation unit 15 generates a background image (hereinafter, referred to as "background thermal image") in the photographing range based on the thermal image group stored in the auxiliary storage device 102 in the predetermined time T1.

For example, when there are a plurality of photographed images included in a visible image group or a thermal image group (hereinafter, when the visible image group and the thermal image group are not distinguished, simply referred to as "photographed image group"), a background image (background visible image and background thermal image) may be generated for each image group using the average value or the median value of the pixel values (RGB) of each photographed image group as the pixel values of each pixel. When there is one photographed image included in the photographed image group, the photographed image is regarded as a background image. By doing so, it is possible to remove a person who has passed temporarily from the background image, and it is possible to generate a background image which is an image composed of only objects that remain in the photographing range for a long time. Many studies have been conducted on a method of dynamically creating a background from images photographed for a certain period of time, and the method of generating a background image in the first embodiment is not limited to a predetermined method.

The predetermined time T1 is a time interval corresponding to the time t1 in FIG. 1, and includes the time t1.

When the background visible image and the background thermal image are generated, step S105 and subsequent steps are executed. It should be noted that steps S101 to S104 and step S105 do not have to be executed synchronously. For example, step S105 and the subsequent steps may be started in response to an instruction different from the execution instruction of steps S101 to S104.

In step S105, the visible image acquisition unit 11 and the thermal image acquisition unit 14 wait for the elapse of a predetermined time T2. The predetermined time T2 is, for example, the elapsed time from the time t2 to the time t3 in FIG. 2.

When the predetermined time T2 elapses (Yes in S105), the visible image acquisition unit 11 acquires a visible image (hereinafter referred to as "target visible image") input from the visible light camera 21, and the thermal image acquisition unit 14 acquires a thermal image (hereinafter, referred to as "target thermal image") input from the thermal camera 22 (S106). It is desirable that the target visible image and the target thermal image are images taken at the same time (or almost at the same time).

In the subsequent step S107, the difference visible image generation unit 13 compares the background visible image generated by the background visible image generation unit 12 with the target visible image by the background subtraction method, and extracts a difference region (a region different from the background visible image) with respect to the background visible image from the target visible image to thereby generate a difference image showing the difference (hereinafter referred to as "difference visible image"). The difference thermal image generation unit 16 compares the background thermal image generated by the background thermal image generation unit 15 with the target thermal image according to the background subtraction method, and extracts a difference region (a region different from the background thermal image) with respect to the background thermal image to generate a difference image (hereinafter, referred to as "difference thermal image") indicating the difference. If the difference in pixel values with respect to the background image is equal to or greater than a certain threshold value, the pixels are different from the background, and if not, the pixels are the same as the background. Then, for example, a binary image in which the pixel value of the pixel different from the background is 1 and the pixel value of the same pixel as the background is 0 is generated as the difference images (difference visible image and difference thermal image). Further, the difference images are sent to the heat trace region extraction unit 17.

Subsequently, the heat trace region extraction unit 17 compares the difference visible image with the difference thermal image to extract the heat trace region in the photographing range (S108).

When extracting a region dissimilar to the difference visible region of the difference thermal image, the similarity determination of the difference region of each difference image may be used. For example, the heat trace region extraction unit 17 first labels (extracts the connecting region) each binary image which is a difference visible image or a difference thermal image. Next, the heat trace region extraction unit 17 compares the degrees of overlap of one or more difference regions (hereinafter, referred to as "difference visible region") obtained by labeling the difference visible image for each of one or more difference regions (hereinafter referred to as "difference thermal region") obtained by labeling the difference thermal images. Specifically, the heat trace region extraction unit 17 counts whether the difference regions to be compared match each other on a pixel-by-pixel basis, and if the match rate is less than a certain threshold value, it is determined that the two difference regions compared are dissimilar. The heat trace region extraction unit 17 extracts a difference thermal region that is dissimilar to any of the difference visible regions as a heat trace region.

The heat trace region extraction unit 17 transmits information indicating the heat trace region and a background visible image to the heat trace region output unit 18. At this time, the heat trace region extraction unit 17 may generate a binary image in which the heat trace region portion is white and the rest is black, and transmit information indicating whether the binary image is the heat trace region to the heat trace region output unit 18 as information indicating the heat trace region. It should be noted that the determination of the similarity of regions is actively performed in the research of pattern matching and the like and is not limited to a predetermined method.

Subsequently, the heat trace region output unit 18 outputs information indicating the heat trace region so that the user can confirm it (S109). Here, the user is a person to be notified of the information indicating the heat trace region. For example, the heat trace region output unit 18 may output an image obtained by combining white pixels of a binary image, which is an example of information indicating a heat trace region, on a background visible image. The output form is not limited to a predetermined form. For example, the display on a display device, the storage in the auxiliary storage device 102, the transmission to a user terminal via a network, and the like may be performed.

Subsequently to step S109, steps S105 and subsequent steps are repeated. Alternatively, step S109 may be executed after steps S105 to S108 are repeated a plurality of times. In this case, the heat trace regions extracted in the plurality of times can be collectively output.

Figure 6:
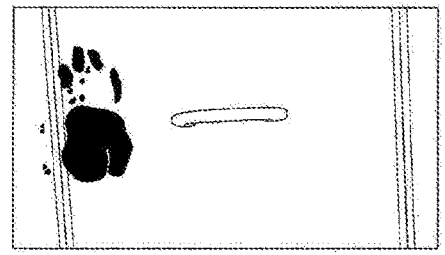
FIG. 6 is a schematic diagram showing an output example of information indicating a heat trace region.

FIG. 6 is a schematic diagram showing an example of an image output by the heat trace region output unit 18. In FIG. 6, the portion touched by a person hand is painted black (however, black is a color for convenience, and the actual color may be a different color such as white). The user can recognize the portion as a heat trace region.

The heat trace region output unit 18 may project a binary image showing the heat trace region to the photographing range in the environment after performing alignment appropriately using a projector or the like. In this case, the heat trace region image is projected on the heat trace portion in the environment, and the portion touched by a person can be directly transmitted to each user in the environment. Using such a method, the user can know the heat trace region, and thus, the user can be urged to take an action such as avoiding touching the heat trace region.

Further, steps S101 to S103 may be executed in parallel with step S105 and subsequent steps. In this case, the background visible image and the background thermal image are updated periodically. Therefore, it can be expected that the resistance to the change in the background with the passage of time will be improved.

In the above, it is assumed that the camera is fixed to an indoor place and heat traces left on a wall or a desk where the place is relatively fixed are extracted. However, the first embodiment can be applied to a moving object as long as the position in the image of an object to be touched by a person can be identified. For example, if a QR code (registered trademark) for identifying the position is attached to the four corners of the seat surface of a chair and the QR code (registered trademark) can be used as a clue to estimate the position on the seat surface, even if the chair moves, the heat traces left on the seat surface can be estimated with the seat surface as a background, and the heat traces can be displayed on the seat surface on the image. Various techniques for estimating the position of an object in an image have been proposed, and the technique is not limited to the use of a QR code (registered trademark).

As described above, according to the first embodiment, it is possible to improve the detection accuracy of the place touched by a person. As a result, for example, it is possible to efficiently sterilize and disinfect a place where viruses such as a new coronavirus or bacteria (hereinafter, referred to as "viruses" for convenience) may be attached.

In the first embodiment, the difference visible image is an example of a first difference image. The difference thermal image is an example of a second difference image. The heat trace region extraction unit 17 is an example of an extraction unit.

Modified Example of First Embodiment

In the first embodiment, in order to explain the difference from the thermal image in an easy-to-understand manner, an example of using a visible image acquired by a visible light camera as an image of an actual object such as a person or an object existing in a photographing range has been described. However, naturally, an image of an actual object may be taken in any wavelength band, and this embodiment will be described as a modified example of the first embodiment.

Figure 7:
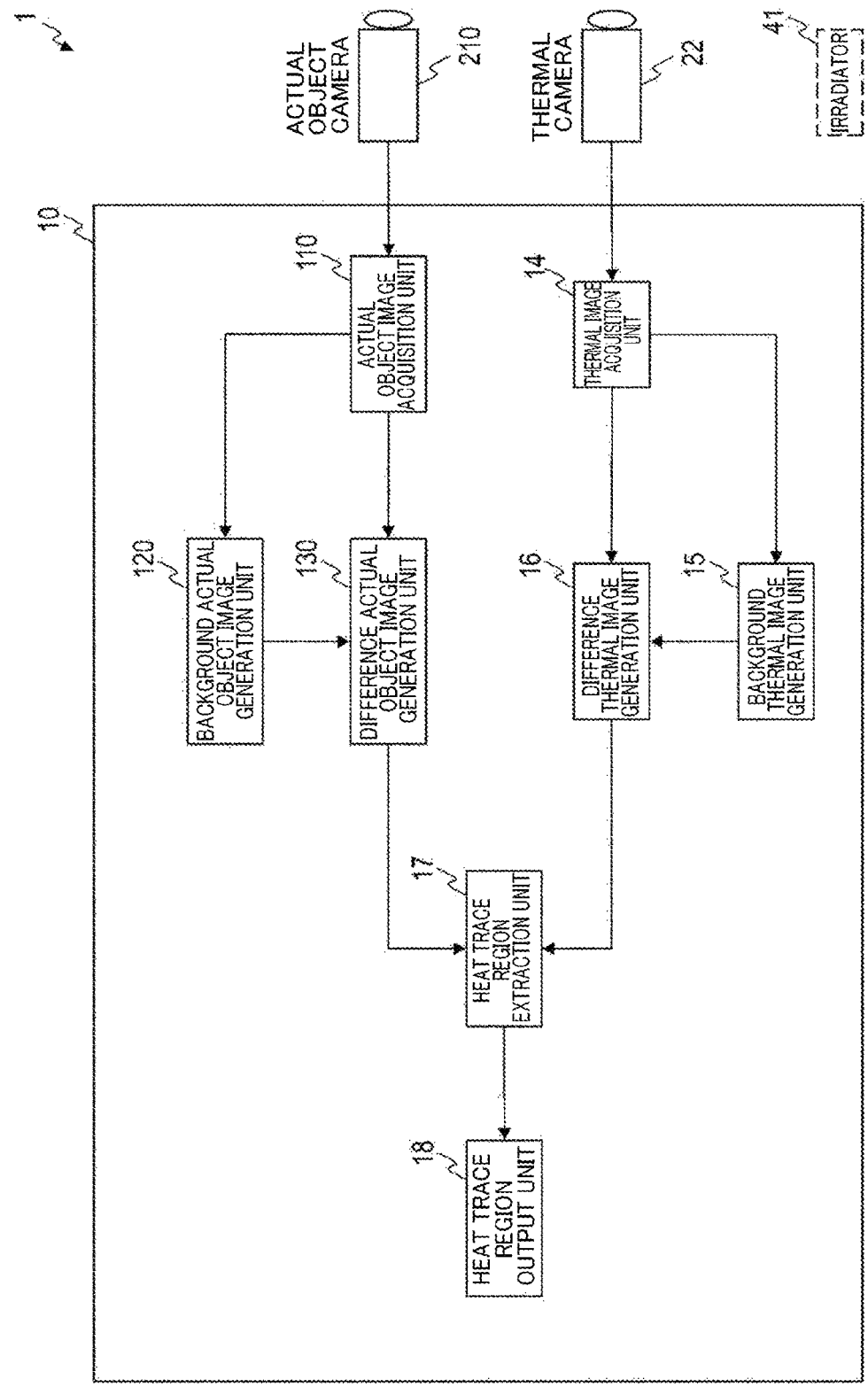
FIG. 7 is a diagram showing a functional configuration example of a heat trace region extraction system 1 and the heat trace region extraction device 10 in a modified example of the first embodiment.

As shown in FIG. 7, the heat trace region extraction system 1 of the modified example of the first embodiment includes a heat trace region extraction device 10, an actual object camera 210, and a thermal camera 22. As shown in FIG. 7, the heat trace region extraction device 10 of the modified example of the first embodiment includes, for example, an actual object image acquisition unit 110, a background actual object image generation unit 120, a difference actual object image generation unit 130, a thermal image acquisition unit 14, a background thermal image generation unit 15, a difference thermal image generation unit 16, a heat trace region extraction unit 17, and a heat trace region output unit 18. The actual object camera 210 and the thermal camera 22 are connected to the heat trace region extraction device 10 of the modified example of the first embodiment, and the images taken by the actual object camera 210 and the thermal camera 22 are input to the heat trace region extraction device 10.

Figure 8:
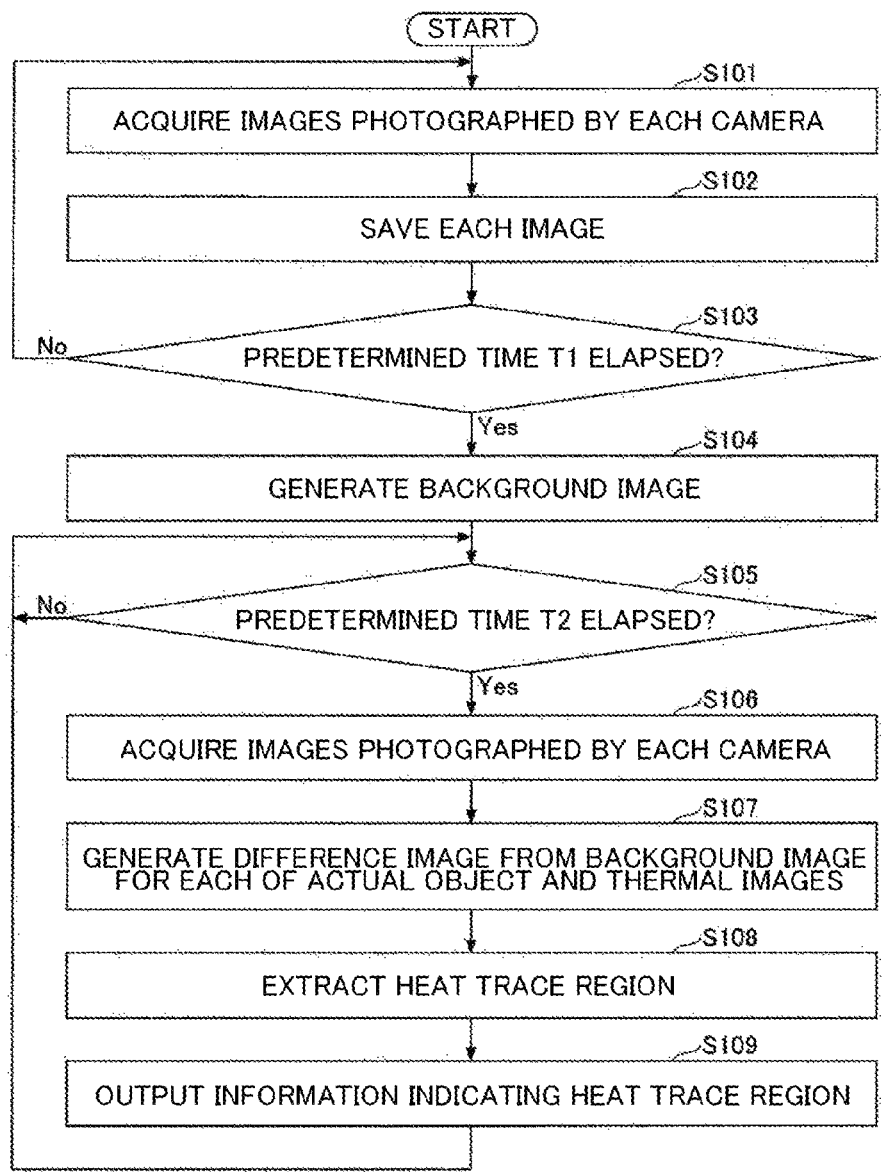
FIG. 8 is a flowchart for explaining an example of a processing procedure executed by a modified example of the first embodiment.

The heat trace region extraction method of the modified example of the first embodiment is realized by each unit of the heat trace region extraction device executing the processing of steps S101 to S109 shown in FIG. 8 and below. Hereinafter, with respect to the modified example of the first embodiment, the same portions as those of the first embodiment will be appropriately omitted, and the portions different from the first embodiment will be mainly described.

<Actual Object Camera 210>

The actual object camera 210 is a camera for photographing an actual object. The actual object camera 210 is the same as the visible light camera 21 of the first embodiment except that the wavelength band of the electromagnetic waves obtained by the actual object camera 210 is not limited to the wavelength band of the visible light. The actual object camera 210 photographs an image of an actual object in a certain photographing range, more specifically, an actual object image which is an image composed of an image of an actual object existing in the photographing range as viewed from the actual object camera 210 side. The actual object image photographed by the actual object camera 210 is input to the actual object image acquisition unit 110.

The wavelength band of the electromagnetic waves photographed by the actual object camera 210 may be any wavelength band in which the actual object can be photographed. A specific example of the wavelength band of the electromagnetic waves obtained by the actual object camera 210 will be described in the fourth embodiment. However, when the wavelength band of the electromagnetic waves obtained by the actual object camera 210 does not include the wavelength band of the electromagnetic waves existing in the photographing range due to illumination or the like, as indicated by a broken line in FIG. 7, the heat trace region extraction system 1 of the modified example of the first embodiment may be provided with an irradiator 41 so that the photographing range may be irradiated with the electromagnetic waves having the wavelength band obtained by the actual object camera 210 using the irradiator 41 that emits an electromagnetic waves having the wavelength band obtained by the actual object camera 210. An actual object is one that has an entity. Examples of an actual object existing in the photographing range are an object existing as a background in the photographing range, a person in the photographing range, and a person entering the photographing range.

<Actual Object Image Acquisition Unit 110>

The actual object image acquisition unit 110 is the same as the visible image acquisition unit 11 of the first embodiment, except that it acquires and outputs an actual object image instead of the visible image. That is, the actual object image acquisition unit 110 acquires the actual object image photographed by the actual object camera 210 (S101) and outputs the acquired actual object image. The actual object image acquired by the actual object image acquisition unit 110 is input to the background actual object image generation unit 120 and/or the difference actual object image generation unit 130.

<Background Actual Object Image Generation Unit 120>

The background actual object image generation unit 120 is the same as the background visible image generation unit 12 of the first embodiment, except that it processes an actual object image instead of the visible image and that it generates and outputs a background actual object image instead of the background visible image. That is, the background actual object image generation unit 120 generates a background actual object image which is an actual object image of the background in the photographing range based on the actual object image acquired by the actual object image acquisition unit 110 (S104) and outputs the generated background actual object image. The actual object image of the background in the photographing range is an image of an object existing as a background in the photographing range, and more specifically, an image composed of images of an object existing as a background in the photographing range, viewed from the actual object camera 210 side. The generated background actual object image is input to the difference actual object image generation unit 130.

<Difference Actual Object Image Generation Unit 130>

The difference actual object image generation unit 130 is the same as the difference visible image generation unit 13 of the first embodiment except that it performs processing on an actual object image instead of a visible image, that it performs processing on a background actual object image instead of a background visible image, and that it generates a difference actual object image instead of a difference visible image. That is, the difference actual object image generation unit 130 generates a difference actual object image which is an image of the difference between the actual object image at a certain time acquired by the actual object image acquisition unit 110 and the background actual object image input from the background actual object image generation unit 120 (S107), and outputs the generated difference actual object image at the certain time. In short, the difference actual object image generation unit 130 generates a difference actual object image which is an image of the difference between the actual object image which is an image of an actual object obtained by photographing a certain range with the actual object camera 210 for photographing an actual object and a background actual object image which is an actual object image of the background of the certain range. The generated difference actual object image is input to the heat trace region extraction unit 17. The difference actual object image generation unit 130 may operate on the actual object image at the time desired to be processed by the heat trace region extraction unit 17, which will be described later.

<Thermal Camera 22>

The thermal camera 22 is the same as the thermal camera 22 of the first embodiment. That is, the thermal camera 22 is a camera for photographing the heat emitted by the actual object. The thermal camera 22 photographs an image of the heat emitted by an actual object in the same photographing range as the actual object camera 210, more specifically, a thermal image which is an image composed of an image of the heat radiated by the actual object existing in the photographing range acquired from the thermal camera 22 side. The thermal image photographed by the thermal camera 22 is input to the thermal image acquisition unit 14.

<Thermal Image Acquisition Unit 14>

The thermal image acquisition unit 14 is the same as the thermal image acquisition unit 14 of the first embodiment. That is, the thermal image acquisition unit 14 acquires the thermal image photographed by the thermal camera 22 (S101) and outputs the acquired thermal image. The thermal image acquired by the thermal image acquisition unit 14 is input to the background thermal image generation unit 15 and/or the difference thermal image generation unit 16.

<Background Thermal Image Generation Unit 15>

The background thermal image generation unit 15 is the same as the background thermal image generation unit 15 of the first embodiment. That is, the background thermal image generation unit 15 generates a background thermal image which is a thermal image of the background in the photographing range based on the thermal image acquired by the thermal image acquisition unit 14 (S104), and outputs the generated background thermal image. The thermal image of the background in the photographing range is an image of the heat emitted by an object existing as the background in the photographing range, and more specifically, an image composed of an image of the heat emitted by the object existing as the background in the photographing range acquired from the thermal camera 22 side. The generated background thermal image is input to the difference thermal image generation unit 16.

<Difference Thermal Image Generation Unit 16>

The difference thermal image generation unit 16 is the same as the difference thermal image generation unit 16 of the first embodiment. That is, the difference thermal image generation unit 16 generates a difference thermal image which is an image of the difference between the thermal image at a certain time acquired by the thermal image acquisition unit 14 and the background thermal image input from the background thermal image generation unit 15 (S107), and outputs the generated difference thermal image at the certain time. In short, the difference thermal image generation unit 16 generates a difference thermal image which is an image of the difference between a thermal image which is an image of the heat emitted by an actual object obtained by photographing the same certain range as the actual object camera 210 by the thermal camera 22 for photographing the heat emitted by the actual object and a background thermal image which is a thermal image of the background in the certain range. The generated difference thermal image is input to the heat trace region extraction unit 17. The difference thermal image generation unit 16 may operate on a thermal image at the time desired to be processed by the heat trace region extraction unit 17, which will be described later.

<Heat Trace Region Extraction Unit 17>

The heat trace region extraction unit 17 is the same as the heat trace region extraction unit 17 of the first embodiment, except that it uses a difference actual object image instead of a difference visible image and that it uses a background actual object image instead of a background visible image. That is, the heat trace region extraction unit 17 extracts a heat trace region by removing the region of the actual object from the thermal image based on the difference actual object image at a certain time generated by the difference actual object image generation unit 130 and the difference thermal image at the certain time generated by the difference thermal image generation unit 16 (S108) and outputs the information indicating the extracted heat trace region at the certain time. Specifically, the heat trace region extraction unit 17 extracts, as a heat trace region, a region which is not similar to any of one or more difference actual object regions among one or more difference thermal regions, using each region different from the background thermal image in the difference actual object image as a difference actual object region and using each region different from the background thermal image in the difference thermal image as a difference thermal region. The information indicating the extracted heat trace region is input to the heat trace region output unit 18. The heat trace region extraction unit 17 generates, for example, a binary image in which the heat trace region portion is white and the rest is black as information indicating the heat trace region, and outputs the generated binary image to the heat trace region output unit 18. The heat trace region extraction unit 17 may also output the background actual object image to the heat trace region output unit 18. The heat trace region extraction unit 17 may operate on the difference actual object image and the difference thermal image at the time desired to be processed by the heat trace region extraction unit 17. The time desired to be processed by the heat trace region extraction unit 17 may be each time at predetermined intervals, or may be a time designated by an operator or the like of the heat trace region extraction device 10.

<Heat Trace Region Output Unit 18>

The heat trace region output unit 18 is the same as the heat trace region output unit 18 of the first embodiment, except that it uses a background actual object image instead of the background visible image. The heat trace region output unit 18 outputs information indicating the heat trace region so that the user can confirm it (S109). For example, the heat trace region output unit 18 outputs an image obtained by combining white pixels of a binary image, which is an example of information indicating a heat trace region, on a background actual object image. For example, the heat trace region output unit 18 projects a binary image showing the heat trace region to the photographing range in the environment after performing alignment appropriately using a projector or the like. The heat trace region output unit 18 may start outputting information indicating the heat trace region when, for example, information indicating the heat trace region is input. The heat trace region output unit 18 may, for example, continue to output information indicating the heat trace region for a predetermined time and end the output after the predetermined time has elapsed. Alternatively, the heat trace region output unit 18 may continue to output the information indicating the heat trace region until it is instructed to end the output by the operator or the like of the heat trace region extraction device 10 and may end the output of the information indicating the heat trace region according to the instruction.

Second Embodiment

The heat trace region extraction device and method of the first embodiment and the modified example of the first embodiment can inform the user of a region where the temperature has risen due to contact with a person, for example, a region where a virus or the like may be attached. However, even in regions where the temperature has risen due to contact with a person, regions that have been disinfected with alcohol or the like after being touched by people are regions where there is a low possibility of being infected with a virus or the like even if they are touched by people. The heat trace region extraction device and method of the second embodiment extract regions having a low possibility of being infected with a virus or the like even if they are touched by such a person.

Figure 9:
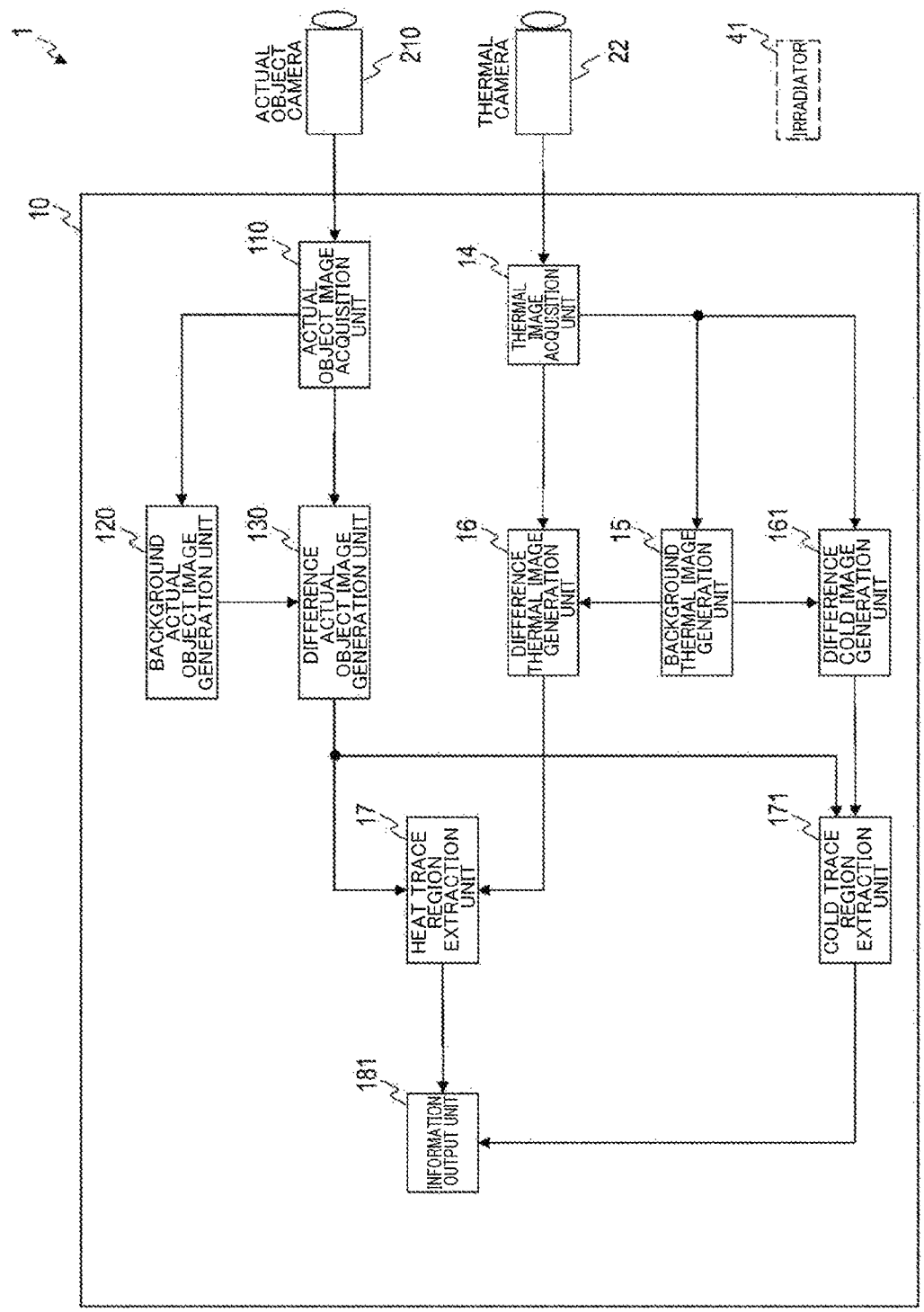
FIG. 9 is a diagram showing a functional configuration example of the heat trace region extraction system 1 and the heat trace region extraction device 10 in the second embodiment.

As shown in FIG. 9, the heat trace region extraction system 1 of the second embodiment includes a heat trace region extraction device 10, an actual object camera 210, and a thermal camera 22. As shown in FIG. 9, the heat trace region extraction device 10 of the second embodiment includes, for example, an actual object image acquisition unit 110, a background actual object image generation unit 120, a difference actual object image generation unit 130, a thermal image acquisition unit 14, a background thermal image generation unit 15, a difference thermal image generation unit 16, a difference cold image generation unit 161, a heat trace region extraction unit 17, a cold trace region extraction unit 171, and an information output unit 181. The actual object camera 210 and the thermal camera 22 are connected to the heat trace region extraction device 10 of the second embodiment, and the images taken by the actual object camera 210 and the thermal camera 22 are input to the heat trace region extraction device 10.

Figure 10:
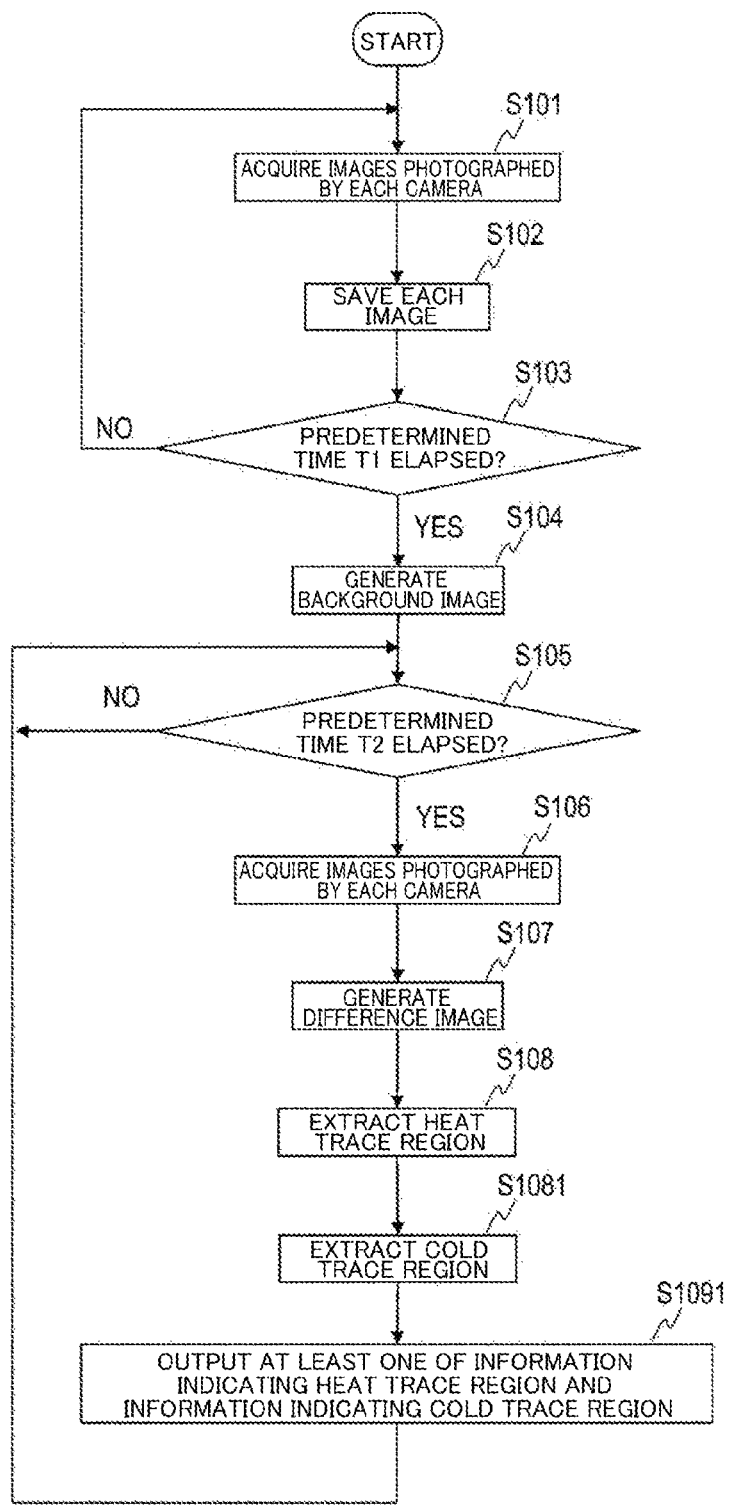
FIG. 10 is a flowchart for explaining an example of a processing procedure executed by the heat trace region extraction device 10 in the second embodiment.

The heat trace region extraction method of the second embodiment is realized by each unit of the heat trace region extraction device executing the processing of steps S101 to S1091 shown in FIG. 10 and below. Hereinafter, portions different from the modified example of the first embodiment will be mainly described. Duplicate explanations will be omitted as appropriate for the same portions as those in the modified example of the first embodiment.

<Actual Object Camera 210>

The actual object camera 210 is the same as the actual object camera 210 of the modified example of the first embodiment. The actual object camera 210 photographs an image of an actual object in a certain photographing range. The actual object image photographed by the actual object camera 210 is input to the actual object image acquisition unit 110.

<Actual Object Image Acquisition Unit 110>

The actual object image acquisition unit 110 is the same as the actual object image acquisition unit 110 of the modified example of the first embodiment. That is, the actual object image acquisition unit 110 acquires the actual object image photographed by the actual object camera 210 (S101) and outputs the acquired actual object image. The actual object image acquired by the actual object image acquisition unit 110 is input to the background actual object image generation unit 120 and/or the difference actual object image generation unit 130.

<Background Actual Object Image Generation Unit 120>

The background actual object image generation unit 120 is the same as the background actual object image generation unit 120 of the modified example of the first embodiment. That is, the background actual object image generation unit 120 generates a background actual object image which is an actual object image of the background in the photographing range based on the actual object image acquired by the actual object image acquisition unit 110 (S104) and outputs the generated background actual object image. The generated background actual object image is input to the difference actual object image generation unit 130.

<Difference Actual Object Image Generation Unit 130>

The difference actual object image generation unit 130 is the same as the difference actual object image generation unit 130 of the modified example of the first embodiment. That is, the difference actual object image generation unit 130 generates a difference actual object image which is an image of the difference between the actual object image at a certain time acquired by the actual object image acquisition unit 110 and the background actual object image input from the background actual object image generation unit 120 (S107), and outputs the generated difference actual object image at the certain time. In short, the difference actual object image generation unit 130 generates a difference actual object image which is an image of the difference between the actual object image which is an image of an actual object obtained by photographing a certain range with the actual object camera for photographing an actual object and a background actual object image which is an actual object image of the background of the certain range. In the second embodiment, the difference actual object image generated by the difference actual object image generation unit 130 is input not only to the heat trace region extraction unit 17 but also to the cold trace region extraction unit 171. The difference actual object image generation unit 130 may operate on an actual object image at the time desired to be processed by the heat trace region extraction unit 17 described later and an actual object image at the time desired to be processed by the cold trace region extraction unit 171 described later.

<Thermal Camera 22>

The thermal camera 22 is the same as the thermal camera 22 of the modified example of the first embodiment. That is, the thermal camera 22 is a camera for photographing the heat emitted by the actual object. The thermal camera 22 photographs an image of the heat emitted by the actual object in the same photographing range as the actual object camera 210. The thermal image photographed by the thermal camera 22 is input to the thermal image acquisition unit 14.

<Thermal Image Acquisition Unit 14>

The thermal image acquisition unit 14 is the same as the thermal image acquisition unit 14 of the modified example of the first embodiment. That is, the thermal image acquisition unit 14 acquires the thermal image photographed by the thermal camera 22 (S101) and outputs the acquired thermal image. The thermal image acquired by the thermal image acquisition unit 14 is input to the background thermal image generation unit 15 and/or the difference thermal image generation unit 16 and the difference cold image generation unit 161.

<Background Thermal Image Generation Unit 15>

The background thermal image generation unit 15 is the same as the background thermal image generation unit 15 of the modified example of the first embodiment. That is, the background thermal image generation unit 15 generates a background thermal image which is a thermal image of the background in the photographing range based on the thermal image acquired by the thermal image acquisition unit 14 (S104), and outputs the generated background thermal image. The generated background thermal image is input to the difference thermal image generation unit 16 and the difference cold image generation unit 161.

<Difference Thermal Image Generation Unit 16>

The difference thermal image generation unit 16 is the same as the difference thermal image generation unit 16 of the modified example of the first embodiment. The difference thermal image generation unit 16 generates a difference thermal image by extracting a region (referred to as "high temperature region") having a high temperature with respect to the background thermal image input from the background thermal image generation unit 15 from the thermal image at a certain time acquired by the thermal image acquisition unit 14 (S107) and outputs the generated difference thermal image at the certain time. That is, the difference thermal image generation unit 16 generates a difference thermal image which is an image including the region of the difference between the thermal image and the background thermal image, the region where the temperature in the thermal image is higher than the temperature in the background thermal image as a high temperature region. For example, the difference thermal image generation unit 16 generates a difference thermal image in which, for each pixel, the pixel value of the difference thermal image is set to 1 in a case where the difference between the pixel value of the thermal image and the pixel value of the background thermal image is equal to or more than a certain threshold value and the temperature indicated by the pixel value of the thermal image is higher than the temperature indicated by the pixel value of the background thermal image, and the pixel value of the difference thermal image is set to 0 in other cases (that is, a case where the temperature indicated by the pixel value of the thermal image is higher than the temperature indicated by the pixel value of the background thermal image and the difference between the pixel value of the thermal image and the pixel value of the background thermal image is less than the certain threshold value and a case where the temperature indicated by the pixel value of the thermal image is not higher than the temperature indicated by the pixel value of the background thermal image). The generated difference thermal image is input to the heat trace region extraction unit 17. The difference thermal image generation unit 16 may operate on a thermal image at the time desired to be processed by the heat trace region extraction unit 17 described later.

<Difference Cold Image Generation Unit 161>

The difference cold image generation unit 161 is the same as the difference thermal image generation unit 16 of the modified example of the first embodiment, except that it generates a difference cold image, which is an image of the difference between the thermal image and the background thermal image and is an image of a region where the temperature is lower than the background, instead of the difference thermal image. The difference cold image generation unit 161 generates a difference cold image by extracting a region (referred to as "low temperature region") having a low temperature with respect to the background thermal image input from the background thermal image generation unit 15 from the thermal image at a certain time acquired by the thermal image acquisition unit 14 (S107) and outputs the generated difference cold image at the certain time. That is, the difference cold image generation unit 161 generates a difference cold image which is an image including the region of the difference between the thermal image and the background thermal image, the region where the temperature in the thermal image is lower than the temperature in the background thermal image as a low temperature region. For example, the difference cold image generation unit 161 generates a difference cold image in which, for each pixel, the pixel value of the difference cold image is set to 1 in a case where the difference between the pixel value of the thermal image and the pixel value of the background thermal image is equal to or more than a certain threshold value and the temperature indicated by the pixel value of the thermal image is lower than the temperature indicated by the pixel value of the background thermal image, and the pixel value of the difference thermal image is set to 0 in other cases (that is, a case where the temperature indicated by the pixel value of the thermal image is lower than the temperature indicated by the pixel value of the background thermal image and the difference between the pixel value of the thermal image and the pixel value of the background thermal image is less than the certain threshold value and a case where the temperature indicated by the pixel value of the thermal image is not lower than the temperature indicated by the pixel value of the background thermal image). The generated difference cold image is input to the cold trace region extraction unit 171. The difference cold image generation unit 161 may operate on a thermal image at the time desired to be processed by the cold trace region extraction unit 171 described later.

<Heat Trace Region Extraction Unit 17>

The heat trace region extraction unit 17 is the same as the heat trace region extraction unit 17 of the modified example of the first embodiment. That is, the heat trace region extraction unit 17 extracts a heat trace region by removing the region of the actual object from the high temperature region included in the difference thermal image based on the difference actual object image generated by the difference actual object image generation unit 130 and the difference thermal image generated by the difference thermal image generation unit 16 (S108) and outputs the information indicating the extracted heat trace region. Specifically, the heat trace region extraction unit 17 extracts, as a heat trace region, a region which is not similar to any of one or more difference actual object regions among one or more difference thermal regions, using each region different from the background thermal image in the difference actual object image as a difference actual object region and using each region different from the background thermal image in the difference thermal image as a difference thermal region. The information indicating the extracted heat trace region is input to the information output unit 181. The heat trace region extracted by the heat trace region extraction unit 17 of the second embodiment is a region in which the temperature has risen due to contact with an actual object, and is, for example, a region touched by a person among objects existing as the background in the photographing range. The heat trace region extraction unit 17 generates, for example, a binary image in which the heat trace region portion is white and the rest is black as information indicating the heat trace region, and outputs the generated binary image to the information output unit 181. The heat trace region extraction unit 17 may operate on the difference actual object image and the difference thermal image at the time desired to be processed by the heat trace region extraction unit 17. The time desired to be processed by the heat trace region extraction unit 17 may be each time at predetermined intervals, or may be a time designated by an operator or the like of the heat trace region extraction device 10.

<Cold Trace Region Extraction Unit 171>

The cold trace region extraction unit 171 is the same as the heat trace region extraction unit 17 of the modified example of the first embodiment except that it performs processing using a difference cold image instead of a difference thermal image, and that it extracts a cold trace region which is a region where the temperature of the heat emitted by the actual object is lowered instead of a heat trace region. That is, the cold trace region extraction unit 171 extracts a cold trace region by removing the region of an actual object from a low temperature region included in the difference cold image based on the difference actual object image generated by the difference actual object image generation unit 130 and the difference cold image generated by the difference cold image generation unit 161 (S1081) and outputs information indicating the extracted cold trace region. Specifically, the cold trace region extraction unit 171 extracts, as a cold trace region, a region which is not similar to any of one or more difference actual object regions among one or more difference cold regions, using each region different from the background thermal image in the difference actual object image as a difference actual object region and using each region different from the background thermal image in the difference cold image as a difference cold region. The information indicating the extracted cold trace region is input to the information output unit 181. The cold trace region extraction unit 171 generates, for example, a binary image in which the cold trace region portion is white and the rest is black as information indicating the cold trace region, and outputs the generated binary image to the information output unit 181. The cold trace region extraction unit 171 may operate on the difference actual object image and the difference cold image at the time desired to be processed by the cold trace region extraction unit 171. The time desired to be processed by the cold trace region extraction unit 171 may be each time at predetermined intervals, or may be a time designated by an operator or the like of the heat trace region extraction device 10.

The cold trace region extracted by the cold trace region extraction unit 171 is a region where the temperature has decreased due to contact with the actual object. When disinfection is performed by wiping with alcohol, the temperature of the wiped region is lowered by the heat of vaporization of alcohol. Even when disinfection is performed by wiping with water, chemicals, and the like instead of alcohol, the temperature of the wiped region generally decreases due to the heat of vaporization. Therefore, the cold trace region extracted by the cold trace region extraction unit 171 is a region where the temperature has decreased due to disinfection with alcohol or the like, and is a region where there is a low possibility of being infected with a virus or the like even if a person touches it. That is, by the processing of the cold trace region extraction unit 171, it is possible to extract a region that is unlikely to be infected with a virus or the like even if it is touched by a person.

Figure 11:
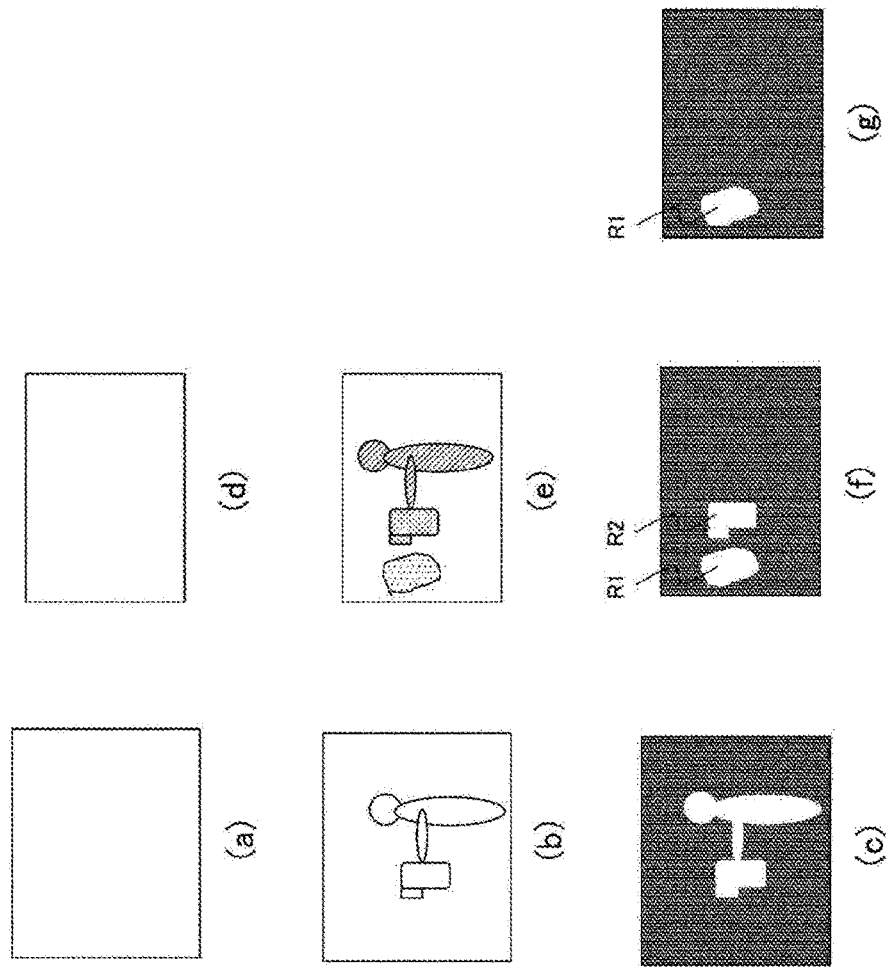
FIG. 11 is a diagram for explaining the second embodiment.

In addition to the disinfected region, the region such as a bottle containing the disinfectant used for disinfection may also appear in the difference cold image obtained by the difference cold image generation unit 161 as the region where the temperature in the thermal image is lower than the temperature in the background thermal image. For example, when the background actual object image is the image of FIG. 11(a), the actual object image is the image of FIG. 11(b), the difference actual object image is the image of FIG. 11(c), and the background thermal image is the image of FIG. 11(d) and the thermal image is the image of FIG. 11(e), the difference cold image obtained by the difference cold image generation unit 161 may be the image of FIG. 11(f). In the difference cold image of FIG. 11(f), not only the disinfected region R1 but also the bottle region R2 appears as a region where the temperature has decreased. Even in such a case, by the process of the cold trace region extraction unit 171, that is, by the process of removing the region of the actual object shown in the difference actual object image from the low temperature region shown in the difference cold image, only the disinfected region R1 can be extracted as a cold trace region as shown in 11(g).

<Information Output Unit 181>

The information output unit 181 uses at least the information indicating the cold trace region to output at least the information indicating the cold trace region so that the user can confirm it (S1091). The information output unit 181 operates as in the first and second examples below, for example.

<<First Example of Information Output Unit 181>>

The information output unit 181 of the first example uses and outputs the information indicating the heat trace region and the information indicating the cold trace region so that the user can confirm at least one of the information indicating the heat trace region and the information indicating the cold trace region. More specifically, the information output unit 181 of the first example continues to output the information indicating the heat trace region once extracted by the heat trace region extraction unit 17 so that the user can confirm it, determines whether the heat trace region overlaps with the cold trace region at a time later than the time corresponding to the heat trace region, and stops outputting all or part of the information indicating the heat trace region according to the determination result. That is, the information output unit 181 of the first example starts outputting the information indicating the heat trace region when the heat trace region is extracted by the heat trace region extraction unit 17, determines whether the cold trace region overlaps with the heat trace region when the cold trace region is extracted by the cold trace region extraction unit 171, and ends the output of all or part of the information indicating the heat trace region when it is determined that they overlap. Hereinafter, an example of the processing of the information output unit 181 of the first example will be described.

Figure 12:
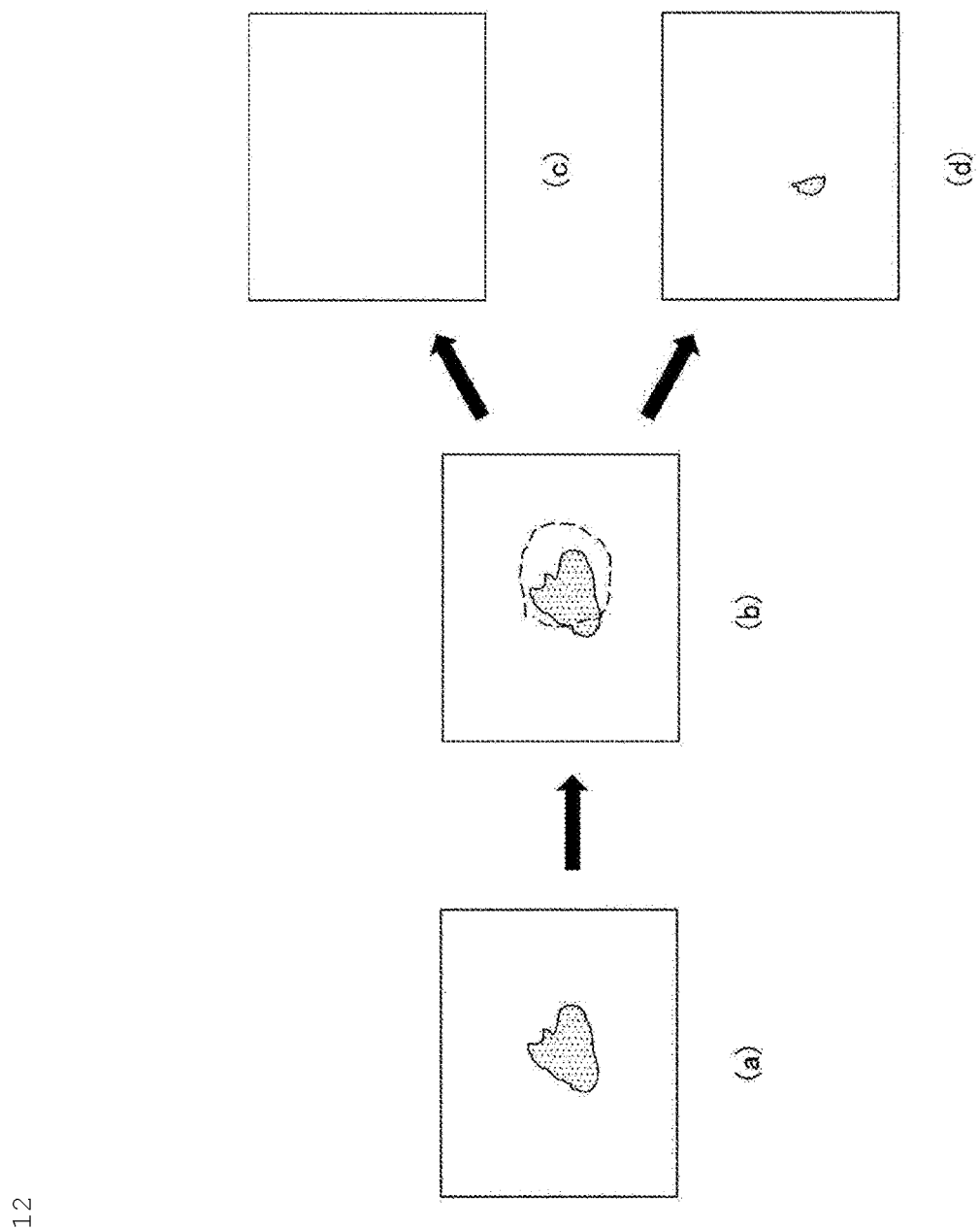
FIG. 12 is a diagram for explaining the second embodiment.

First, when the heat trace region is extracted by the heat trace region extraction unit 17, the information output unit 181 outputs information indicating the heat trace region so that the user can confirm it in the same manner as the heat trace region output unit 18 of the first embodiment. For example, the information output unit 181 displays the information indicating the heat trace region so that the user can confirm it by appropriately aligning a binary image, which is information indicating whether it is a heat trace region as shown in FIG. 12(a), and then projecting it onto a photographing range in the environment. In this example, the information indicating the heat trace region is a binary image. In FIG. 12(a) and FIG. 12(b) used in the following description, the region painted with the dot pattern is a heat trace region, and the region painted with white is not a heat trace region.

After that, it is assumed that a cold trace region is extracted by the cold trace region extraction unit 171. An example of this cold trace region is indicated by a broken line in FIG. 12(b). The broken line in FIG. 12(b) indicates the edge of the cold trace region. The region surrounded by the broken line in FIG. 12(b) is the cold trace region. When the cold trace region is extracted by the cold trace region extraction unit 171, the information output unit 181 determines whether the heat trace region overlaps with the cold trace region for each of the heat trace regions extracted in the past.

For example, the information output unit 181 calculates the match rate, which is an index indicating how much of the heat trace region is the cold trace region. For example, the match rate=(the number of pixels in which the heat trace region and the cold trace region overlap)/(the number of pixels in the heat trace region). The information output unit 181 stops the output of the information indicating the heat trace region for the heat trace region where the match rate is equal to or higher than a predetermined threshold value. For example, when the heat trace region and the cold trace region are in the state illustrated in FIG. 12(b), the binary image illustrated in FIG. 12(c) is projected onto the photographing range in the environment. That is, the display of the heat trace region is stopped. This predetermined threshold value is a real number close to 1, for example 0.9. As described above, the information output unit 181 may stop the output of all the information indicating the heat trace region according to the determination result of whether the heat trace region overlaps with the cold trace region.

For example, the information output unit 181 stops the output of information indicating the heat trace region for the portion of the heat trace region that overlaps with the cold trace region. For example, when the heat trace region and the cold trace region are in the state illustrated in FIG. 12(b), the binary image illustrated in FIG. 12(d) is projected onto the photographing range in the environment. In other words, the information output unit 181 may display only the region excluding the region where the heat trace region overlaps with the cold trace region from the heat trace region. As described above, the information output unit 181 may stop the output of a part of the information indicating the heat trace region according to the determination result of whether the heat trace region overlaps with the cold trace region.

Even if a person infected with a virus or the like touches a region in the past and the virus or the like has been attached to the region, the region disinfected with alcohol is a region where there is a low possibility of being infected with the virus or the like even if it is touched by people. The heat trace region is a region where the temperature has risen due to contact with a person, and is considered to be a region where a virus or the like may be attached. On the other hand, the cold trace region is a region where the temperature has decreased due to disinfection with alcohol or the like, and is considered to be a region where there is low possibility of being infected with the virus or the like even if it is touched by people. As in the first example of the information output unit 181, the information indicating the heat trace region once extracted is continuously output so that the user can confirm it, but the output of a part of the information indicating the heat trace region is stopped according to the determination result of whether the heat trace region overlaps with a cold trace region extracted later. By doing so, the user can be presented with only the region that may be infected with a virus or the like.

<<Second Example of Information Output Unit 181>>

The information output unit 181 of the second example uses and outputs the information indicating the cold trace region so that the user can confirm the information indicating the cold trace region. More specifically, the information output unit 181 of the second example outputs only the information indicating the cold trace region extracted by the cold trace region extraction unit 171 so that the user can confirm it. For example, the information output unit 181 outputs an image obtained by combining white pixels of a binary image, which is an example of information indicating a cold trace region, on a background actual object image. For example, the information output unit 181 projects a binary image showing a cold trace region onto a photographing range in the environment after performing alignment appropriately using a projector or the like. As a result, the user can know the region where there is a low possibility of being infected with a virus or the like even if the user touches the region disinfected with alcohol or the like. The information output unit 181 may start outputting the information indicating the cold trace region, for example, when the information indicating the cold trace region is input.

When the information output unit 181 performs the operation of the second example, the heat trace region extraction device 10 does not need to obtain information indicating the heat trace region. In such a case, the heat trace region extraction device 10 may not include the difference thermal image generation unit 16 and the heat trace region extraction unit 17. The heat trace region extraction device 10 that does not include the difference thermal image generation unit 16 and the heat trace region extraction unit 17 can be said to be a cold trace region extraction device.

Third Embodiment

The heat trace region extraction device and method of the first embodiment can inform the user of a region where the temperature has risen due to contact with a person and a region where a virus or the like may be attached. However, even a region where the temperature has risen due to contact with a person with a low body temperature is a region where it is unlikely that the virus or the like is attached since it is unlikely that the touched person is infected with a virus or the like. On the other hand, a region where the temperature has risen due to contact with a person with a high body temperature is a region where there is a high possibility that the virus or the like is attached because the touched person is likely to be infected with the virus or the like. From these facts, in order to more appropriately inform the user of the region where a virus or the like may be attached, it may be better if it is possible to identify a person or the body temperature that causes the heat trace corresponding to the heat trace region as well as extracting the heat trace region which is the region where the temperature has risen due to contact with a person. The heat trace region extraction device and method of the third embodiment identify the temperature that causes the heat trace corresponding to the heat trace region.

Figure 13:
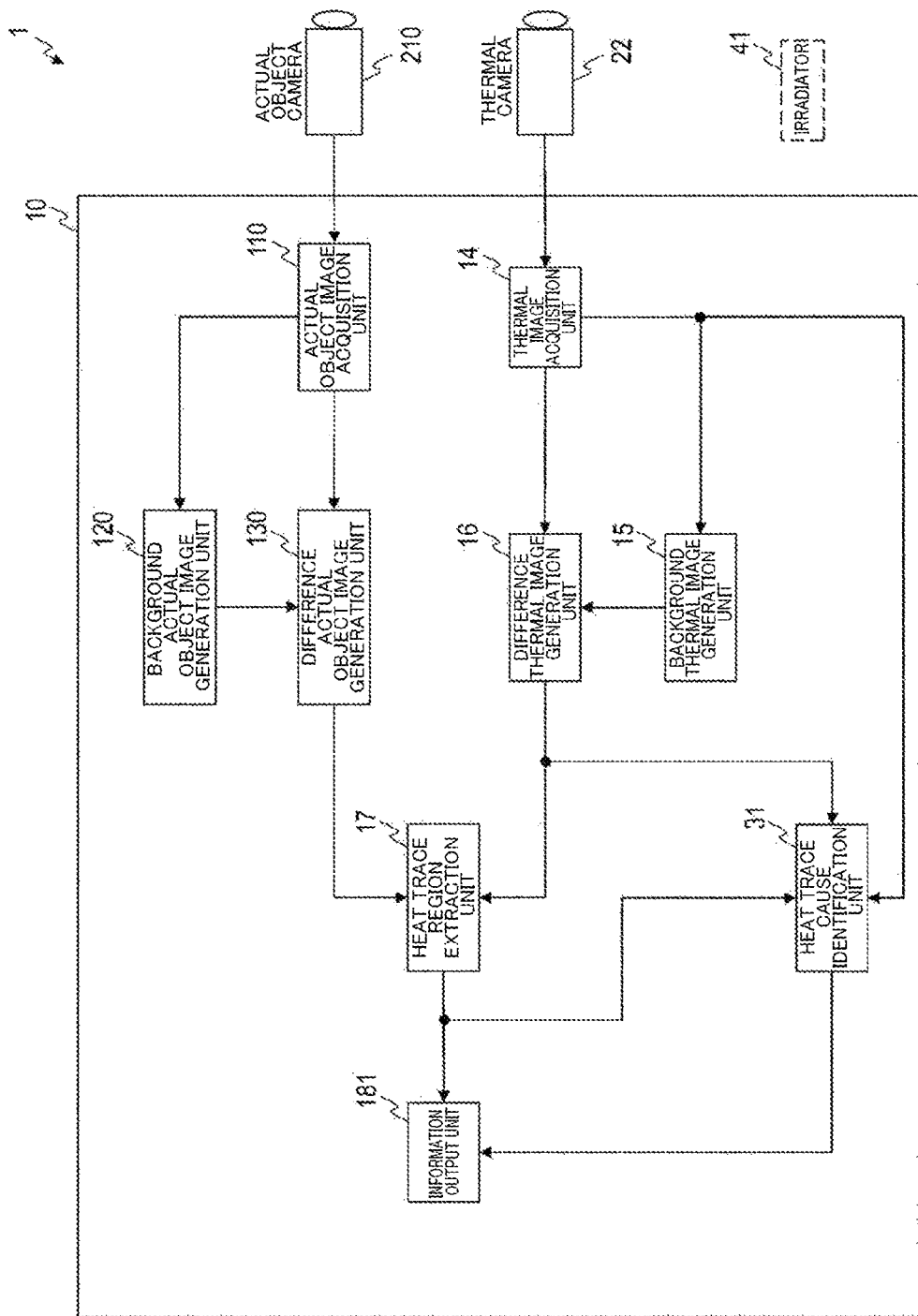
FIG. 13 is a diagram showing a functional configuration example of the heat trace region extraction system 1 and the heat trace region extraction device 10 in the third embodiment.

As shown in FIG. 13, the heat trace region extraction system 1 of the third embodiment includes a heat trace region extraction device 10, an actual object camera 210, and a thermal camera 22. As shown in FIG. 13, the heat trace region extraction device 10 of the third embodiment includes, for example, an actual object image acquisition unit 110, a background actual object image generation unit 120, a difference actual object image generation unit 130, a thermal image acquisition unit 14, a background thermal image generation unit 15, a difference thermal image generation unit 16, a heat trace region extraction unit 17, a heat trace cause identification unit 31, and an information output unit 181. The actual object camera 210 and the thermal camera 22 are connected to the heat trace region extraction device 10 of the third embodiment, and the images taken by the actual object camera 210 and the thermal camera 22 are input to the heat trace region extraction device 10.

Figure 14:
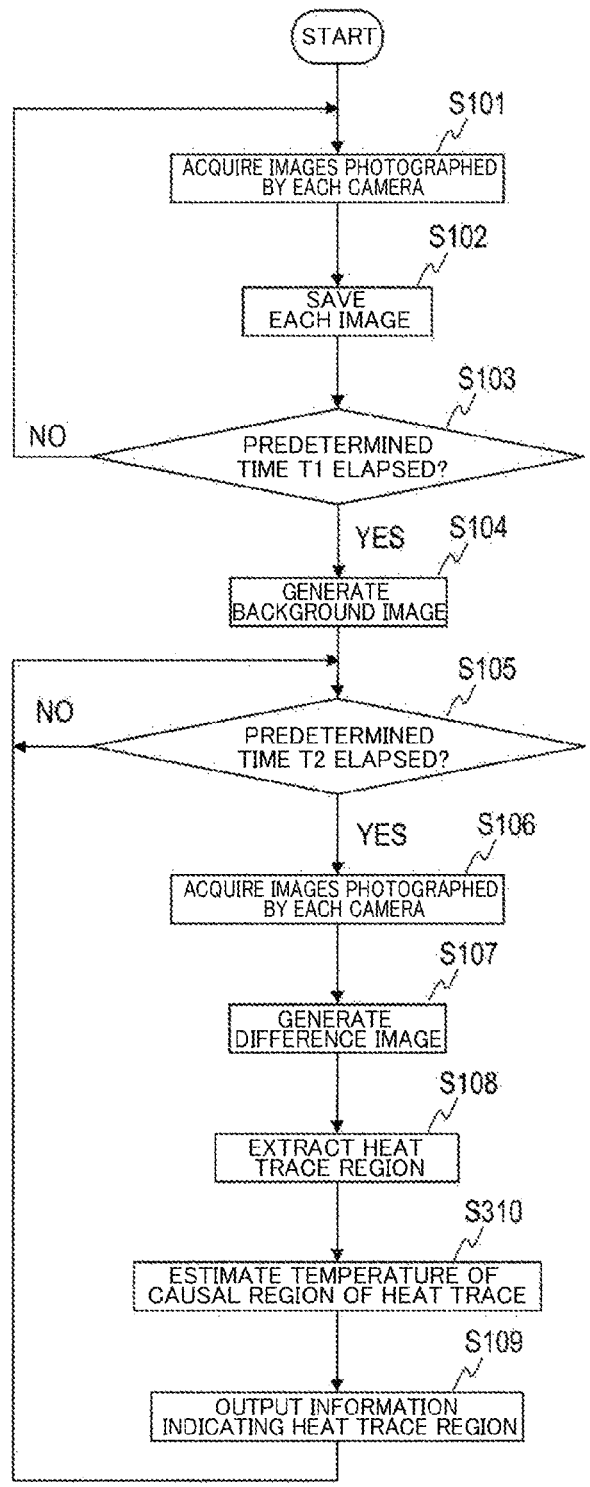
FIG. 14 is a flowchart for explaining an example of a processing procedure executed by the heat trace region extraction device 10 in the third embodiment.

The heat trace region extraction method of the third embodiment is realized by each unit of the heat trace region extraction device executing the processing of steps S101 to S109 shown in FIG. 14 and below. Hereinafter, portions different from the modified example of the first embodiment will be mainly described. Duplicate explanations will be omitted as appropriate for the same portions as those in the modified example of the first embodiment.

The actual object camera 210, the actual object image acquisition unit 110, the background actual object image generation unit 120, the difference actual object image generation unit 130, the thermal camera 22, the thermal image acquisition unit 14, the background thermal image generation unit 15, and the difference thermal image generation unit 16 are the same as the actual object camera 210, the actual object image acquisition unit 110, the background actual object image generation unit 120, the difference actual object image generation unit 130, the thermal camera 22, the thermal image acquisition unit 14, the background thermal image generation unit 15, and the difference thermal image generation unit 16 of the modified example of the first embodiment, respectively. However, the difference thermal image generated by the difference thermal image generation unit 16 and the thermal image acquired by the thermal image acquisition unit 14 are further input to the heat trace cause identification unit 31.

In addition to the operation of the heat trace region extraction unit 17 of the modified example of the first embodiment, the heat trace region extraction unit 17 generates and outputs a difference thermal region image showing one difference thermal region as a difference and a heat trace region image showing only one heat trace region as a difference and outputs time information corresponding to each heat trace region image. The heat trace region extraction unit 17 assigns a file name to each image and also outputs the file name. The difference thermal region image, the heat trace region image, the time information corresponding to the heat trace region image, and the file name of each image obtained by the heat trace region extraction unit 17 are input to the heat trace cause identification unit 31.

When one difference thermal region is obtained, the heat trace region extraction unit 17 generates an image showing the one difference thermal region as a difference as a difference thermal region image. Further, when p is a positive integer of 2 or more and p difference thermal regions separated from each other are obtained, the heat trace region extraction unit 17 generates p images each showing only one difference thermal region different among the p difference thermal regions as a difference as difference thermal region images. The heat trace region extraction unit 17 generates, for example, a binary image in which the pixel value of each pixel in the difference thermal region is 1 and the pixel value of each pixel in a region other than the difference thermal region is as a difference thermal region image.

When one heat trace region is obtained, the heat trace region extraction unit 17 generates an image showing the one heat trace region as a difference as a heat trace region image. Further, when q is a positive integer of 2 or more and q heat trace regions separated from each other are obtained, the heat trace region extraction unit 17 generates q images each showing only one heat trace region different among the q heat trace regions as a region as heat trace region images. The heat trace region extraction unit 17 generates, for example, a binary image in which the pixel value of each pixel in the heat trace region is 1 and the pixel value of each pixel in a region other than the heat trace region is 0 as a heat trace region image.

In the third embodiment, a heat trace table is created based on the heat trace region image and the time information corresponding to the heat trace region image obtained by the heat trace region extraction unit 17. The heat trace table is stored in the auxiliary storage device 102. An example of a heat trace table is shown in FIG. 15. In the heat trace table of FIG. 15, records for each heat trace region at each time extracted by the heat trace region extraction unit 17 are recorded, and the records for each heat trace region include the time corresponding to the heat trace region image, the file name of the heat trace region image, and the group ID to which the heat trace region belongs. The group ID to which each heat trace region belongs in the heat trace table is generated by the heat trace cause identification unit 31 described later.

The heat trace region at the time "2021-08-10 10:50: 48.000" in FIG. 15 is the heat trace region extracted by the process corresponding to the latest time "2021-08-10 10:50: 48.000" in the heat trace region extraction unit 17 and is not yet processed by the heat trace cause identification unit 31. Therefore, the group ID to which the heat trace region belongs is not assigned to the record of the heat trace region at the time "2021-08-10 10:50:48.000" in FIG. 15. The heat trace cause identification unit 31 performs a process of identifying the cause of the corresponding heat trace on the heat trace region extracted by the process corresponding to the latest time in the heat trace region extraction unit 17 and assigns a group ID during the process.

<Heat Trace Cause Identification Unit 31>

The heat trace cause identification unit 31 performs a first identification process of identifying a heat trace region due to a cause different from a cause by which the heat trace region extracted by the process corresponding to the past time became a heat trace among the heat trace regions extracted by the process corresponding to the latest time, a second identification process of identifying a causal region which is a region which became the cause by which the heat trace region identified in the first identification process became the heat trace using the difference thermal image extracted by the process corresponding to the past time, of the heat trace region extraction unit 17, and a third identification process of identifying a temperature of the causal region identified in the second identification process from a thermal image corresponding to the difference thermal image used for identifying the causal region (S310). The temperature of the causal region identified in the third identification process (that is, the temperature of the causal region of the heat trace corresponding to each heat trace region) is input to the information output unit 181.

Specifically, the second identification process performed by the heat trace cause identification unit 31 is a process of identifying a difference thermal image of a time (past time) earlier than the difference thermal image corresponding to the heat trace region identified in the first identification process, the difference thermal image satisfying a condition that a region corresponding to the heat trace region identified in the first identification process is included, as a difference thermal region, in all difference thermal images ranging from the difference thermal images corresponding to the heat trace region identified in the first identification process to the difference thermal images of the earlier time (past time), and the difference thermal image including a difference thermal region in which a region different from the region corresponding to the heat trace region identified in the first identification process is connected to a region corresponding to the heat trace region identified in the first identification process, and identifying the different region in the identified difference thermal image as a causal region which became the cause of the heat trace corresponding to the heat trace region identified in the first identification process.

Hereinafter, an example of the processing of the heat trace cause identification unit 31 will be described. In the following description, the heat trace region extracted by the heat trace region extraction unit 17 in the process corresponding to the latest time is referred to as a new heat trace region. In the following description, the heat trace region extracted by the process corresponding to the time earlier than the latest time is also referred to as an old heat trace region.

The heat trace cause identification unit 31 performs the following processing each time the heat trace region is extracted by the processing corresponding to the latest time in the heat trace region extraction unit 17. That is, the heat trace cause identification unit 31 performs the following processing on each new heat trace region.

First, the heat trace cause identification unit 31 determines a group to which the new heat trace region belongs by performing the processing of steps S3101 to S3106 shown in FIG. 16 and below.

The heat trace cause identification unit 31 selects one old heat trace region latest among the old heat trace regions that have not yet been selected (S3101), and the processing proceeds to step S3102. The heat trace cause identification unit 31 selects, for example, one old heat trace region in which the group ID recorded in the heat trace table is different from the group IDs of the old heat trace regions selected so far and the time recorded in the heat trace table is the latest. Hereinafter, the old heat trace region selected by the heat trace cause identification unit 31 is abbreviated as "selected old heat trace region".

The heat trace cause identification unit 31 determines whether the difference between the time corresponding to the new heat trace region and the time corresponding to the selected old heat trace region is equal to or less than a predetermined time (S3102). For example, the heat trace cause identification unit 31 may determine whether the difference between the time included in the record of the new heat trace region recorded in the heat trace table and the time included in the record of the selected old heat trace region recorded in the heat trace table is equal to or less than a predetermined time. The predetermined time is longer than an average time in which the temperature of the heat trace region decreases and becomes the same as the temperature of the background. For example, the predetermined time is 10 seconds.

When the heat trace cause identification unit 31 determines in step S3102 that the difference between the time corresponding to the new heat trace region and the time corresponding to the selected old heat trace region is equal to or less than the predetermined time, the processing proceeds to step S3103. When it is determined in step S3102 that the difference between the time corresponding to the new heat trace region and the time corresponding to the selected old heat trace region is not less than or equal to the predetermined time, the processing proceeds to step S3106. The processing of step S3106, which is a process performed when it is determined in step S3102 that the difference between the time corresponding to the new heat trace region and the time corresponding to the selected old heat trace region is not equal to or less than the predetermined time, will be described later.

When the difference between the corresponding time of the new heat trace region and the corresponding time of the selected old heat trace region is less than or equal to the predetermined time, the heat trace cause identification unit 31 determines whether the size of the region not included in the selected old heat trace region in the new heat trace region is equal to or smaller than a predetermined size (S3103). The heat trace cause identification unit 31 may make the determination of step S3103 using, for example, a heat trace region image of a file identified by the file name of a new heat trace region recorded in the heat trace table and a heat trace region image of a file identified by the file name of a selected old heat trace region recorded in the heat trace table.

When the heat trace cause identification unit 31 determines in step S3103 that the size of the region not included in the selected old heat trace region in the new heat trace region is not equal to or smaller than the predetermined size, the processing proceeds to S3101. When the heat trace cause identification unit 31 determines in step S3103 that the size of the region not included in the selected old heat trace region in the new heat trace region is equal to or less than the predetermined size, the processing proceeds to step S3104.

When the size of the region not included in the selected old heat trace region in the new heat trace region is less than or equal to the predetermined size, the heat trace cause identification unit 31 determines whether the temperature corresponding to the new heat trace region is lower than the temperature corresponding to the selected old heat trace region (S3104). The temperature corresponding to the new heat trace region can be obtained from the thermal image corresponding to the new heat trace region. For example, the heat trace cause identification unit 31 calculates the average value of the temperature indicated by each pixel included in the region corresponding to the new heat trace region in the thermal image corresponding to the heat trace region image of the new heat trace region and uses the average value as the temperature corresponding to the new heat trace region. Similarly, the temperature corresponding to the selected old heat trace region can be obtained from the thermal image corresponding to the selected old heat trace region. For example, the heat trace cause identification unit 31 calculates the average value of the temperature indicated by each pixel included in the region corresponding to the selected old heat trace region in the thermal image corresponding to the heat trace region image of the selected old heat trace region and uses the average value as the temperature corresponding to the selected old heat trace region.

When the heat trace cause identification unit 31 determines in step S3104 that the temperature corresponding to the new heat trace region is not lower than the temperature corresponding to the selected old heat trace region, the processing proceeds to step S3101. When the heat trace cause identification unit 31 determines in step S3104 that the temperature corresponding to the new heat trace region is lower than the temperature corresponding to the selected old heat trace region, the processing proceeds to step S3105.

When the temperature corresponding to the new heat trace region is lower than the temperature corresponding to the selected old heat trace region, the heat trace cause identification unit 31 determines that the new heat trace region belongs to the same group as the selected old heat trace region (S3105). In this case, the heat trace cause identification unit 31 records, for example, the same number as the group ID of the record of the selected old heat trace region recorded in the heat trace table as the group ID of the record of the new heat trace region in the heat trace table.

When the size of the region not included in the selected old heat trace region in the new heat trace region is less than or equal to the predetermined size, and the temperature corresponding to the new heat trace region is lower than the temperature corresponding to the selected old heat trace region, the new heat trace region is considered to be the region of the selected old heat trace region, which is reduced with the passage of time and in which the temperature has decreased. Therefore, in this case, the heat trace cause identification unit 31 may determine that the cause of the heat trace corresponding to the new heat trace region is the same as the cause of the heat trace corresponding to the selected old heat trace region. This determination is performed in the processes from step S3103 to step S3105.

When it is determined in the processing of step S3102 that the difference between the time corresponding to the new heat trace region and the time corresponding to the selected old heat trace region is not less than or equal to the predetermined time, the heat trace cause identification unit 31 determines that the new heat trace region belongs to a new group (S3106). That is, when it is determined in the processing of step S3102 that the difference between the time corresponding to the new heat trace region and the time corresponding to the selected old heat trace region is not equal to or less than the predetermined time, the heat trace cause identification unit 31 determines that the new heat trace region is a heat trace region due to a new cause different from the cause by which the heat trace region extracted by the process corresponding to the past time became the heat trace. In this case, the heat trace cause identification unit 31 records, for example, a number different from the group ID of the record of any one of the old heat trace regions recorded in the heat trace table as the group ID of the record of the new heat trace region in the heat trace table.

In general, heat traces often disappear within seconds of the generation of heat traces. Therefore, if the difference between the time corresponding to the new heat trace region and the time corresponding to the latest old heat trace region is not equal to or less than the predetermined time, the new heat trace region is considered to be generated based on a cause different from the cause of the heat trace corresponding to the old heat trace region. The determination based on this idea is the processing of step S3102 and step S3106.

Figure 16:
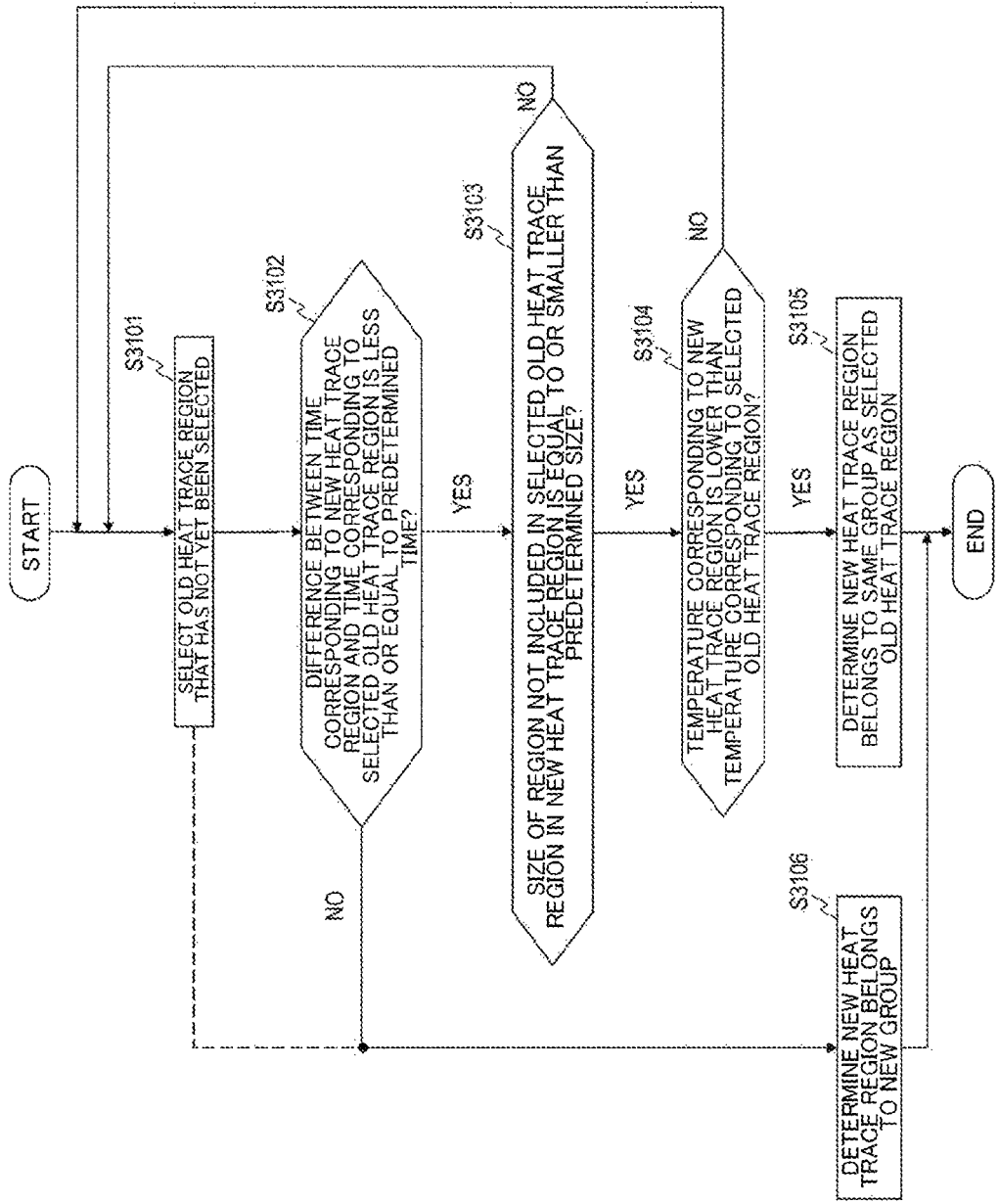
FIG. 16 is a diagram for explaining the third embodiment.

As indicated by the broken line in FIG. 16, the heat trace cause identification unit 31 determines that the new heat trace region belongs to a new group even if there is no old heat trace region that has not yet been selected in the processing of step S3101 performed first, in other words, even if there is no old heat trace region to be selected (S3106). In this case, the heat trace cause identification unit 31 records, for example, an arbitrary number in the heat trace table as the group ID of the record of the new heat trace region.

For example, when it is determined that the heat trace region at the time "2021-08-10 10:50:48.000" in the heat trace table of FIG. 15 belongs to a new group, "28" which is a new group ID is assigned to the heat trace region.

Figure 17:
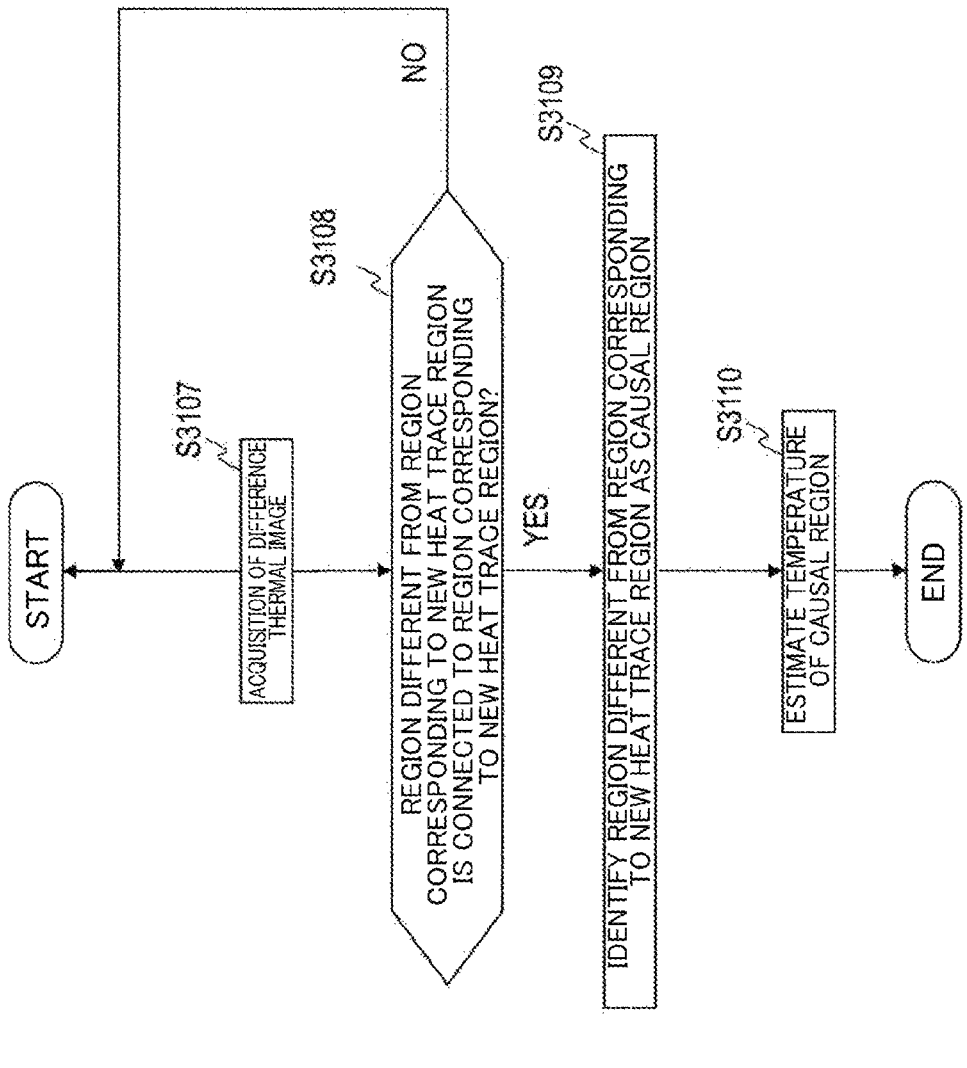
FIG. 17 is a diagram for explaining the third embodiment.

When it is determined that the new heat trace region belongs to a new group, the heat trace cause identification unit 31 performs the processing of steps S3107 to S3110 shown in FIG. 17 and below to identify the causal region which is a region that caused the heat trace of the new heat trace region and estimate the temperature of the causal region of the heat trace.

The heat trace cause identification unit 31 acquires the latest difference thermal image of the difference thermal images that have not been selected yet among the difference thermal images of the time earlier than the time corresponding to the new heat trace region determined to belong to a new group (S3107) and the processing proceeds to step S3108. For example, in the first processing of step S3107, the heat trace cause identification unit 31 acquires a difference thermal image one hour before the time corresponding to the new heat trace region. For example, with k being a positive integer of 2 or more, in the (k−1)-th and subsequent processing of step S3107, the heat trace cause identification unit 31 acquires a difference thermal image one hour before the time of the difference thermal image acquired in the k-th processing of step S3107.

In the processing of steps S3107 to S3110, the heat trace cause identification unit 31 may use the difference thermal region image in which the difference thermal region is included in the region corresponding to the new heat trace region instead of the difference thermal image. When the heat trace cause identification unit 31 uses the difference thermal region image instead of the difference thermal image, the difference thermal image generated by the difference thermal image generation unit 16 may not be input to the heat trace cause identification unit 31.

The heat trace cause identification unit 31 determines whether the acquired difference thermal image includes a difference thermal region in which a region different from the region corresponding to the new heat trace region is connected to the region corresponding to the new heat trace region (S3108). When the heat trace cause identification unit 31 determines that the acquired difference thermal image does not include a difference thermal region in which a region different from the region corresponding to the new heat trace region is connected to the region corresponding to the new heat trace region, the processing proceeds to step S3107. When the heat trace cause identification unit 31 determines that the acquired difference thermal image includes a difference thermal region in which a region different from the region corresponding to the new heat trace region is connected to the region corresponding to the new heat trace region, the processing proceeds to step S3109.

When the difference thermal image includes a difference thermal region in which a region different from the region corresponding to the new heat trace region (hereinafter, referred to as "connecting region" for convenience) is connected to the region corresponding to the new heat trace region, the heat trace cause identification unit 31 identifies the connecting region as the causal region that caused the heat trace of the new heat trace region (S3109), and the processing proceeds to step S3110.

The heat trace cause identification unit 31 estimates the temperature of the causal region from the temperature of the region corresponding to the causal region of the thermal image corresponding to the difference thermal image (S3110). For example, the heat trace cause identification unit 31 calculates the average value of the temperature indicated by each pixel included in the region corresponding to the causal region in the thermal image corresponding to the difference thermal image, and uses the average value as the temperature of the causal region. The heat trace cause identification unit 31 may use the median or maximum value of the temperature indicated by each pixel included in the region corresponding to the causal region in the thermal image corresponding to the difference thermal image as the temperature of the causal region.

In this way, the heat trace cause identification unit 31 performs the following processing using the extracted heat trace region as the new heat trace region, and using the heat trace region extracted at a time earlier than the time when the new heat trace region is extracted as the old heat trace region. (1) When the difference between the time corresponding to the new heat trace region and the time corresponding to the old heat trace region is less than or equal to a predetermined time, the size of a region not included in the old heat trace region in the new heat trace region is equal to or less than a predetermined size, and the temperature corresponding to the new heat trace region is lower than the temperature corresponding to the old heat trace region, it is determined that the new heat trace region belongs to the same group as the old heat trace region. That is, it is determined that the cause by which the new heat trace region became the heat trace is the same as the cause by which the old heat trace region became the heat trace. (2) In other case, it is determined that the new heat trace region belongs to a new group. That is, the cause by which the new heat trace region became the heat trace is different from the cause by which the old heat trace region became the heat trace. The heat trace cause identification unit 31 identifies a difference thermal image of a time earlier than the difference thermal image corresponding to the new heat trace region determined to belong to the new group, the difference thermal image satisfying a condition that a region corresponding to the new heat trace region determined to belong to the new group is included as a difference thermal region, in all difference thermal images ranging from the difference thermal image corresponding to the new heat trace region determined to belong to the new group to the difference thermal image of the earlier time, the difference thermal image including a difference thermal region in which a region different from the region corresponding to the new heat trace region is connected to the region corresponding to the new heat trace region, and identifies the different region in the identified difference thermal image as a causal region which is a region that caused the heat trace corresponding to the new heat trace region. The heat trace cause identification unit estimates the temperature of the region identified as the causal region from the thermal image corresponding to the difference thermal image used for identifying the causal region.

Figure 18:
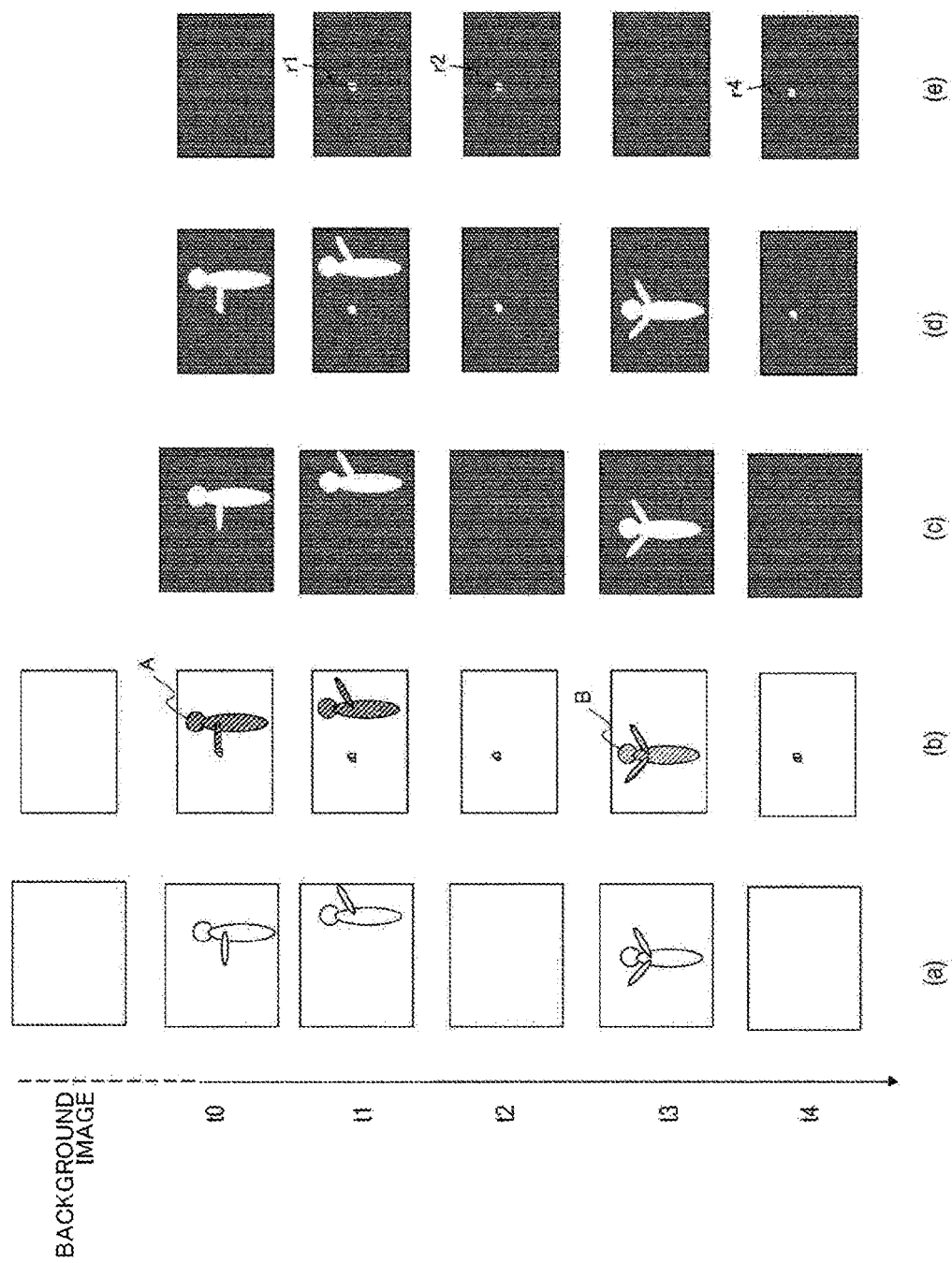
FIG. 18 is a diagram for explaining the third embodiment.

Hereinafter, an example of the processing of the heat trace cause identification unit 31 will be described with reference to FIG. 18. FIG. 18(a) is a schematic diagram of a background actual object image and an actual object image at each time, FIG. 18(b) is a schematic diagram of a background thermal image and a thermal image at each time, FIG. 18(c) is a schematic diagram of a difference actual object image at each time, FIG. 18(d) is a schematic diagram of a difference thermal image at each time, and FIG. 18(e) is a schematic diagram of an image showing a heat trace region at each time.

At time t0, it is assumed that there is a region where the person A touches the wall and the temperature has risen. Further, it is assumed that the person A moves away from the wall at time t1 and the person A goes out of the photographing range at time t2. After that, it is assumed that the person B crosses the photographing range at time t3 and the person B goes out of the photographing range at time t4. Assuming that using $\tau=1, 2, 4$, the heat trace region extracted at time $t\tau$ will be referred to as the heat trace region $r\tau$. At time t3, the heat trace region is not extracted because the person B overlaps with the region where the heat trace regions r1 and r2 were.

First, an example of identifying the region that caused the heat trace of the heat trace region r1 at time t1 will be described. In this example, the heat trace region r1 is referred to as a new heat trace region r1. In this example, at time t1, since the heat trace region is not extracted at the time earlier than the time t1, the information of the old heat trace region does not exist. Therefore, since the heat trace cause identification unit 31 cannot select the old heat trace region (S3101), it is determined that the new heat trace region r1 belongs to a new group (S3106). The heat trace cause identification unit 31 acquires a difference thermal image at time t0, which is the latest difference thermal image before time t1 (S3107), and determines whether the difference thermal image at time t0 includes a difference thermal region in which a region different from the region corresponding to the new heat trace region r1 is connected to the region corresponding to the new heat trace region r1 (S3108). In this example, in the difference thermal image at time t0 (the image at time t0 in FIG. 18(d)), the region different from the region corresponding to the new heat trace region r1 (the region of person A) is included as a difference thermal region connected to the region corresponding to the new heat trace region r1. Therefore, the heat trace cause identification unit 31 identifies the region of the person A in the difference thermal image at time t0 as the region that caused the heat trace in the new heat trace region r1 (S3109).

Next, an example of identifying the region that caused the heat trace of the heat trace region r2 at time t2 will be described. In this example, the heat trace region r2 is referred to as a new heat trace region r2.

First, the heat trace cause identification unit 31 selects the heat trace region r1 extracted at time t1 as an old heat trace region (S3101). Hereinafter, the heat trace region r1 will be referred to as an old heat trace region r1. The heat trace cause identification unit 31 determines whether the difference between the time t2 corresponding to the new heat trace region r2 and the time t1 corresponding to the old heat trace region r1 is equal to or less than a predetermined time (S3102). The heat trace cause identification unit 31 also determines whether the size of the region not included in the old heat trace region r1 in the new heat trace region r2 is equal to or smaller than a predetermined size (S3103). The heat trace cause identification unit 31 also determines whether the temperature corresponding to the new heat trace region r2 is lower than the temperature corresponding to the old heat trace region r1 (S3104).

In this example, it is assumed that the difference between the time t2 corresponding to the new heat trace region r2 and the time t1 corresponding to the old heat trace region r1 is less than or equal to the predetermined time, the size of the region not included in the old heat trace region r1 in the new heat trace region r2 is equal to or smaller than the predetermined size, and the temperature corresponding to the new heat trace region r2 is lower than the temperature corresponding to the old heat trace region r1. Therefore, the heat trace cause identification unit 31 determines that the new heat trace region r2 belongs to the same group as the old heat trace region r1 (S3105).

The fact that the new heat trace region r2 belongs to the same group as the old heat trace region r1 means that the cause of the heat trace in the new heat trace region r2 is the same as the cause of the heat trace in the old heat trace region r1. The region that caused the heat trace of the old heat trace region r1 has already been identified as the region of person A in the above-mentioned example at time t1. Therefore, the region that caused the heat trace of the new heat trace region r2 is the region of person A.

Next, an example of identifying the region that caused the heat trace of the heat trace region r4 at time t4 will be described. In this example, the heat trace region r4 is referred to as a new heat trace region r4. In this example, there are two persons who are candidates for the cause of the heat trace corresponding to the new heat trace region r4. These two persons are person A and person B. Therefore, whether the cause of the heat trace corresponding to the new heat trace region r4 is the person A or the person B is a problem.

First, the heat trace cause identification unit 31 selects the heat trace region r2 extracted at time t2 as the old heat trace region (S3101). Hereinafter, the heat trace region r2 will be referred to as an old heat trace region r2. The heat trace cause identification unit 31 determines whether the difference between the time t4 corresponding to the new heat trace region r4 and the time t2 corresponding to the old heat trace region r2 is less than or equal to a predetermined time (S3102). The heat trace cause identification unit 31 also determines whether the size of the region not included in the old heat trace region r2 in the new heat trace region r4 is equal to or smaller than the predetermined size (S3103). The heat trace cause identification unit 31 also determines whether the temperature corresponding to the new heat trace region r4 is lower than the temperature corresponding to the old heat trace region r2 (S3104).

In this example, it is assumed that the difference between the time t4 corresponding to the new heat trace region r4 and the time t2 corresponding to the old heat trace region r2 is less than or equal to the predetermined time, the size of the region not included in the old heat trace region r2 in the new heat trace region r4 is equal to or smaller than the predetermined size, and the temperature corresponding to the new heat trace region r4 is lower than the temperature corresponding to the old heat trace region r2. Therefore, the heat trace cause identification unit 31 determines that the new heat trace region r4 belongs to the same group as the old heat trace region r2 (S3105).

The fact that the new heat trace region r4 belongs to the same group as the old heat trace region r2 means that the new heat trace region r4 belongs to the same group as the old heat trace region r1 assuming that it is already identified in the above-mentioned example at time t2 that the old heat trace region r2 belongs to the same group as the old heat trace region r1. That is, the cause of the heat trace in the new heat trace region r4 is the same as the cause of the heat trace in the old heat trace region r1. The region that caused the heat trace of the old heat trace region r1 has already been identified as the region of person A in the above-mentioned example at time t1. Therefore, the region that caused the heat trace of the new heat trace region r4 is the region of person A.

As in this example, even if there are two or more persons who are candidates for the cause of the heat trace in the heat trace region, the person who causes the heat trace in the heat trace region can be identified more appropriately by the processing of the heat trace cause identification unit 31 described above.

<Information Output Unit 181>

The information output unit 181 receives the information indicating the heat trace region extracted by the heat trace region extraction unit 17, and the temperature of the causal region of the heat trace corresponding to each heat trace region identified by the heat trace cause identification unit 31.

The information output unit 181 outputs the information indicating the heat trace region input from the heat trace region extraction unit 17 so that the user can confirm it in an expression method determined according to the temperature of the causal region input from the heat trace cause identification unit 31 (S109). For example, the information output unit 181 displays the information indicating the heat trace region extracted by the heat trace region extraction unit 17 in an expression method determined according to the temperature identified by the heat trace cause identification unit 31. For example, the information output unit 181 projects an image or video obtained by processing a binary image, in which the heat trace region portion, which is information indicating the heat trace region, is white and the rest is black, in accordance with the temperature of the causal region input from the heat trace cause identification unit 31, to a photographing range.

An example of the expression method according to the temperature of the causal region is an expression method that is stronger as the temperature increases. The expression method that is stronger as the temperature increases is, in other words, an expression method that attracts the user's attention as the temperature increases. An example of the expression method that is stronger as the temperature increases is an expression method in which, when the temperature of the heat trace region is higher than a predetermined threshold value, display of information indicating that it is the heat trace region portion or the heat trace region blinks, and the speed of blinking the display of the information indicating that it is the heat trace region portion or the heat trace region increases as the temperature increases. For example, this example can be realized when the information output unit 181 projects a video onto the photographing range such that the brightness of the video is set to 0 in a region other than the heat trace region and is set to a predetermined brightness in the heat trace region where the temperature is equal to or lower than a predetermined threshold value, and the brightness changes periodically in the time direction like a rectangular wave between the predetermined brightness and 0 at a higher frequency as the temperature increases in the heat trace region where the temperature is higher than the predetermined threshold value.

Another example of the expression method that is stronger as the temperature increases is an expression method in which when the temperature of the heat trace region is higher than a predetermined threshold value, the color of display of information indicating that it is the heat trace region portion or the heat trace region changes, and the speed of changing the color of the display of information indicating that it is the heat trace region portion or the heat trace region increases as the temperature of the heat trace region increases. Another example of the expression method that is stronger as the temperature increases is an expression method in which when the temperature of the heat trace region is higher than a predetermined threshold value, the display of information indicating that it is the heat trace region portion or the heat trace region vibrates, and the frequency of vibrating of the display of information indicating that it is the heat trace region portion or the heat trace region increases as the temperature of the heat trace region increases. Another example of the expression method that is stronger as the temperature increases is an expression method in which the display of information indicating that it is the heat trace region portion or the heat trace region is brighter as the temperature of the heat trace region increases. Another example of the expression method that is stronger as the temperature increases is an expression method in which the duration of the portion of the display indicating that it is the heat trace region portion or the heat trace region increases as the temperature of the heat trace region increases.

Another example of the expression method that differs depending on the temperature of the causal region is an expression method of displaying the numerical value of the temperature together with the information indicating that it is the heat trace region portion or the heat trace region. Another example of the expression method that differs depending on the temperature of the causal region is an expression method in which the information indicating that it is the heat trace region portion or the heat trace region is indicated by a different color depending on the temperature. In an example of this expression method, when the temperature of the heat trace region is higher than a predetermined threshold value, information indicating that it is the heat trace region portion or the heat trace region is displayed in a first color, and in other cases, the information indicating that it is the heat trace region portion or the heat trace region is displayed in a second color. For example, the first color is red and the second color is blue.

The information output unit 181 may create a group information table illustrated in FIG. 19 and display information with reference to the group information table and the heat trace table stored in the auxiliary storage device 102. The group information table of FIG. 19 stores records corresponding to each heat trace region, and each record includes a group ID to which each heat trace region belongs, the temperature of a region that caused the heat trace of each heat trace region, and an ID for identifying a display method corresponding to each heat trace region. In this example, the ID that identifies the display method is represented by a number that increases as the temperature increases. When the ID is displayed in a stronger expression as the temperature increases, the information output unit 181 may use an expression method that becomes stronger as the ID for identifying the display method increases.

Fourth Embodiment

The heat trace region extraction device and method of the first embodiment can inform the user of a region where the temperature has risen due to contact with a person, in other words, a region where a virus such as a new coronavirus may be attached by projecting the region using a projector or the like. However, when the projector projects with visible light, the visible light camera 21 also photographs the visible light projected by the projector, and a visible image is obtained in which light and shade due to the light projected by the projector is superimposed on a person, an object, or the like existing in the photographing range. In particular, when the output of the projector is large, the light and shade due to the light projected by the projector is strongly superimposed on the image of a person or an object existing in the photographing range. Therefore, there is a possibility that the heat trace region cannot be appropriately extracted by the heat trace region extraction device and method of the first embodiment.

In the heat trace region extraction device and method of the fourth embodiment, an actual object camera 210 that does not photograph the wavelength band of visible light projected by the projector is used as a camera for photographing an actual object instead of the visible light camera 21. Therefore, the wavelength band of the electromagnetic waves obtained by the actual object camera 210 and the wavelength band of the visible light projected by the projector do not overlap, and the light projected by the projector does not affect the extraction of the heat trace region.

Figure 20:
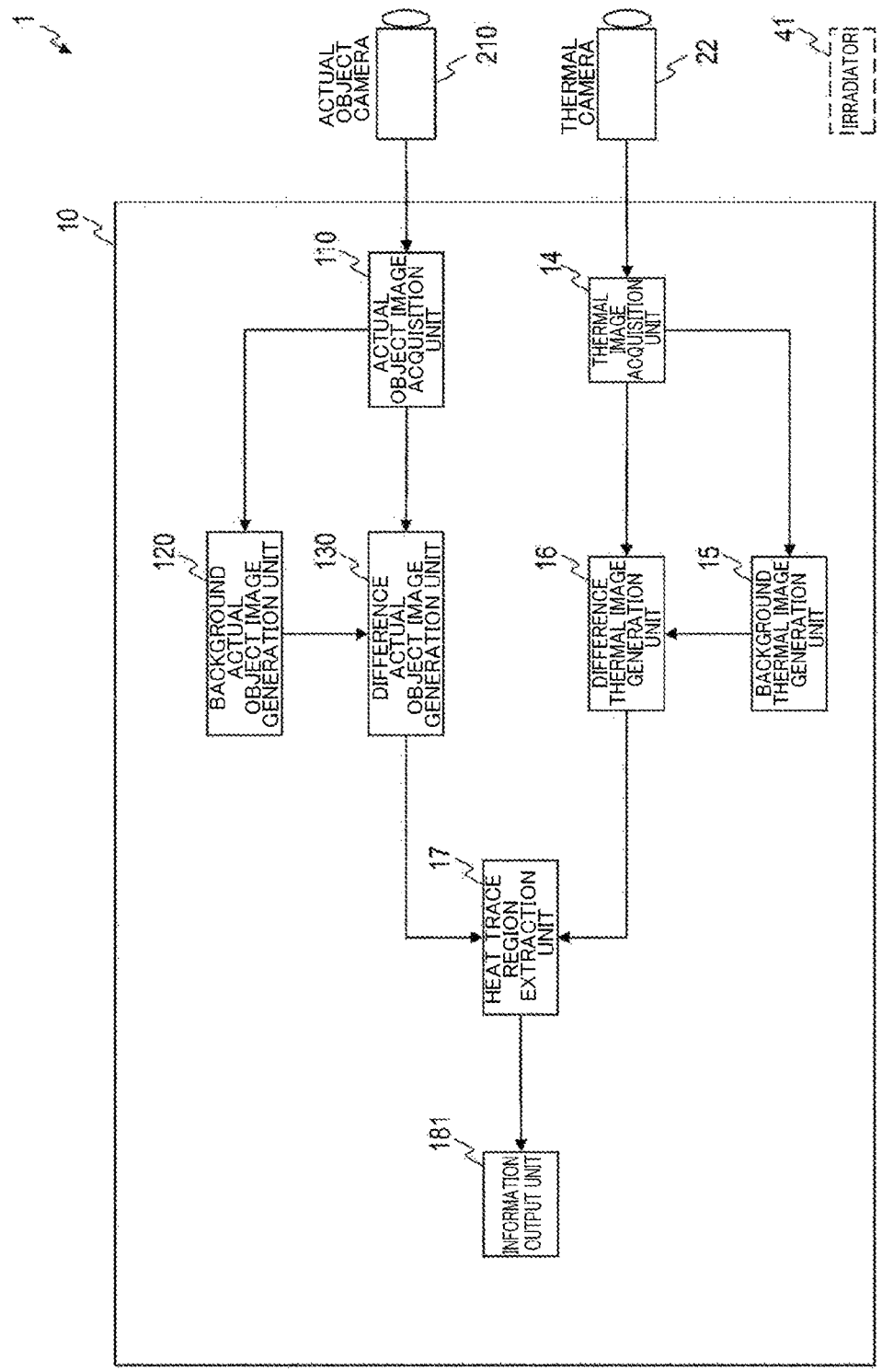
FIG. 20 is a diagram showing a functional configuration example of the heat trace region extraction system 1 and the heat trace region extraction device 10 in the fourth embodiment.

As shown in FIG. 20, the heat trace region extraction system 1 of the fourth embodiment includes a heat trace region extraction device 10, an actual object camera 210, and a thermal camera 22. As shown in FIG. 20, the heat trace region extraction device 10 of the fourth embodiment includes, for example, an actual object image acquisition unit 110, a background actual object image generation unit 120, a difference actual object image generation unit 130, a thermal image acquisition unit 14, a background thermal image generation unit 15, a difference thermal image generation unit 16, a heat trace region extraction unit 17, and an information output unit 181. The actual object camera 210 and the thermal camera 22 are connected to the heat trace region extraction device 10 of the fourth embodiment, and the images taken by the actual object camera 210 and the thermal camera 22 are input to the heat trace region extraction device 10.

Figure 21:
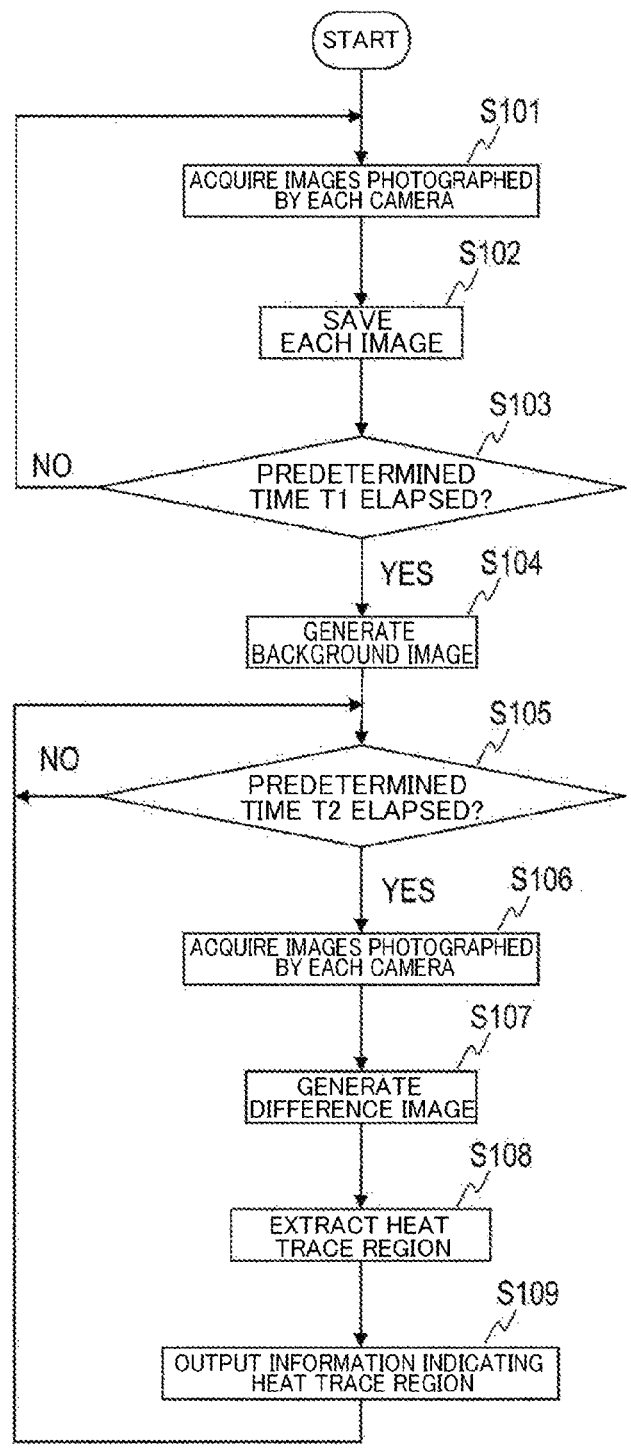
FIG. 21 is a flowchart for explaining an example of a processing procedure executed by the heat trace region extraction device 10 in the fourth embodiment.

The heat trace region extraction method of the fourth embodiment is realized by each unit of the heat trace region extraction device executing the processing of steps S101 to S109 shown in FIG. 21 and below. Hereinafter, the portions different from the first embodiment to the third embodiment will be mainly described. Duplicate explanations will be omitted for the same portions as those of the first to third embodiments.

The actual object camera 210, the actual object image acquisition unit 110, the background actual object image generation unit 120, the difference actual object image generation unit 130, the thermal camera 22, the thermal image acquisition unit 14, the background thermal image generation unit 15, the difference thermal image generation unit 16, and the heat trace region extraction unit 17 are the same as the actual object camera 210, the actual object image acquisition unit 110, the background actual object image generation unit 120, the difference actual object image generation unit 130, the thermal camera 22, the thermal image acquisition unit 14, the background thermal image generation unit 15, the difference thermal image generation unit 16, and the heat trace region extraction unit 17 of the modified example of the first embodiment, respectively.

However, the actual object camera 210 is a camera in which the wavelength band of the electromagnetic waves to be photographed satisfies the requirements described later. Further, it is assumed that the information indicating the heat trace region extracted by the heat trace region extraction unit 17 is input to the information output unit 181.

In the fourth embodiment, the information output unit 181 has a function of a projector. Similarly to the heat trace region output unit 18 of the first embodiment, the information output unit 181 having the projector function projects information indicating the heat trace region with visible light to a certain range which is a photographing range (S109).

In the fourth embodiment, the actual object camera 210 is a camera that does not photograph the wavelength band of visible light projected by the projector. That is, the actual object camera 210 is a camera that photographs electromagnetic waves in a wavelength band different from the wavelength band of visible light projected by the projector. Further, naturally, the actual object camera 210 is a camera that does not photograph the heat emitted by the actual object. That is, the actual object camera 210 is a camera that photographs electromagnetic waves in a wavelength band different from the wavelength band of the electromagnetic waves obtained by the thermal camera 22. Further, naturally, since the information output unit 181 projects visible light, the information output unit 181 projects visible light in a wavelength band different from the wavelength band of the electromagnetic waves obtained by the thermal camera 22.

From the above, the wavelength band of the electromagnetic waves obtained by the actual object camera 210, the wavelength band of the electromagnetic waves obtained by the thermal camera 22, and the wavelength band of the visible light projected by the information output unit 181 do not overlap. The wavelength band is a range of wavelengths in which the intensity of electromagnetic waves or visible light is equal to or higher than a predetermined intensity.

For example, the wavelength band of visible light projected by the information output unit 181 is set to 400 nm to 780 nm, the wavelength band of electromagnetic waves obtained by the actual object camera 210 is set to the wavelength band in the near-infrared region (for example, 780 nm to 2500 nm), and the wavelength band of the electromagnetic waves obtained by the thermal camera 22 is set to 8 μm to 14 μm, which is the wavelength band of heat rays (far-infrared region). The wavelength band in the near-infrared region may be 800 nm to 1000 nm. The upper limit of the wavelength band of visible light projected by the information output unit 181 may be set to 800 nm, the lower limit of the wavelength band of the electromagnetic waves obtained by the actual object camera 210 may be set to 850 nm, and the wavelength band of the electromagnetic waves obtained by the thermal camera 22 may be set to 8 μm to 14 μm.

For example, the wavelength band of visible light projected by the information output unit 181 may be set to 400 nm to 600 nm, the lower limit of the wavelength band of electromagnetic waves obtained by the actual object camera 210 may be set to 600 nm, which is the wavelength of visible light, and the wavelength band of the electromagnetic waves obtained by the thermal camera 22 may be set to 8 μm to 14 μm. As in this example, if the wavelength bands do not overlap, both the wavelength band of the electromagnetic waves obtained by the actual object camera 210 and the wavelength band of the visible light projected by the information output unit 181 may be the wavelength bands of the visible light.

For example, the wavelength band of visible light projected by the information output unit 181 may be set to 600 nm to 800 nm, the wavelength band of the electromagnetic waves obtained by the actual object camera 210 may be set to 400 nm to 600 nm, and the wavelength band of the electromagnetic waves obtained by the thermal camera 22 may be set to 8 μm to 14 μm. As in this example, as long as the wavelength bands do not overlap, the order of the wavelength band of visible light projected by the information output unit 181 and the wavelength band of the electromagnetic waves obtained by the actual object camera 210 does not matter. That is, it is not essential that the wavelength band of the electromagnetic waves obtained by the actual object camera 210 is located on the longer wavelength side than the wavelength band of the visible light projected by the information output unit 181. The wavelength band of the visible light projected by the information output unit 181 may be located on the longer wavelength side than the wavelength band of the electromagnetic waves obtained by the actual object camera 210.

The wavelength band may be controlled by a well-known technique. The wavelength band can be controlled by attaching a physical filter for transmitting electromagnetic waves and visible light of a predetermined wavelength band to a lens of the actual object camera 210, a lens of the thermal camera 22, and a projection lens of a projector of the information output unit 181. The wavelength band may be controlled by signal processing. For example, the information output unit 181 may control the wavelength band by filtering the signal generated for projection and projecting an image based on the filtered signal. The actual object camera 210 may control the wavelength band by filtering the signal acquired by the actual object camera 210 and acquiring an actual object image from the filtered signal. Similarly, the thermal camera 22 may control the wavelength band by filtering the signal acquired by the thermal camera 22 and acquiring a thermal image from the filtered signal.

In the heat trace region extraction device and method of the modified example of the first embodiment and the second and third embodiments, the wavelength band of the electromagnetic waves obtained by the actual object camera 210, the wavelength band of the electromagnetic waves obtained by the thermal camera 22, and the wavelength band of the visible light projected by the information output unit 181 may be prevented from overlapping with each other in the same manner as described above. That is, the fourth embodiment also includes an embodiment in which the heat trace region extraction device and method of the modified example of the first embodiment and the second and third embodiments are configured such that the wavelength band of the electromagnetic waves obtained by the actual object camera 210, the wavelength band of the electromagnetic waves obtained by the thermal camera 22, and the wavelength band of the visible light projected by the information output unit 181 are prevented from overlapping with each other in the same manner as described above.

In this way, since the wavelength band of the electromagnetic waves obtained by the actual object camera 210, the wavelength band of the electromagnetic waves obtained by the thermal camera 22, and the wavelength band of the visible light projected by the information output unit 181 do not overlap with each other, the visible light projected by the information output unit 181 is not photographed by the actual object camera 210. Therefore, the heat trace region extraction device and method of the fourth embodiment can appropriately extract the heat trace region.

If the wavelength band of the electromagnetic waves obtained by the actual object camera 210 does not include the wavelength band of the electromagnetic waves existing in the photographing range due to illumination or the like, the photographing range may be irradiated by the irradiator 41 that emits the electromagnetic waves in the wavelength band obtained by the actual object camera 210. For example, when the wavelength band of the electromagnetic waves obtained by the actual object camera 210 is the wavelength band in the near-infrared region and the illumination in the photographing range is an illumination such as a fluorescent lamp that does not include the wavelength band in the near-infrared region, the photographing range may be irradiated by the irradiator 41 that emits the electromagnetic waves in the wavelength band in the near-infrared region obtained by the actual object camera 210. In this case, the heat trace region extraction system 1 of the fourth embodiment may further include the irradiator 41, for example, as indicated by the broken line in FIGS. 7, 9, 13, and 20.

Fifth Embodiment

In the heat trace region extraction device and method of the first to fourth embodiments, the information output unit 181 may output information indicating the heat trace region in various variations. The heat trace region extraction device and method of the fifth embodiment is the heat trace region extraction device and method of the first to fourth embodiments, in which the information output unit 181 outputs information indicating the heat trace region in various variations. For the sake of simplicity, in the fifth embodiment, the heat trace region output unit 18 of the first embodiment and the modified example of the first embodiment will be referred to as an information output unit 181.

As described above, the information output unit 181 outputs information indicating a heat trace region which is a region of a trace of heat, extracted based on an actual object image which is an image of an actual object, obtained by photographing a certain range with an actual object camera for photographing the actual object and a thermal image which is an image of the heat emitted by the actual object, obtained by photographing a certain range with a thermal camera for photographing the heat emitted by the actual object.

Hereinafter, the portions different from the heat trace region extraction device and method of the first to fourth embodiments will be mainly described. Duplicate explanations will be omitted for the same portions as those in the first to fourth embodiments.

(Variation 1)

The information output unit 181 may display information indicating the heat trace region on a transmissive display. An example of a transmissive display is a transmissive head-mounted display. In this case, the information output unit 181 includes a transmissive display, and detects the position and direction of the transmissive display so that the heat trace region existing in the real space (that is, the photographing range of the actual object camera and the thermal camera) visually recognized by the user through the transmissive display and information indicating the heat trace region displayed on the transmissive display are aligned. As a result, the user can visually recognize the information indicating the heat trace region displayed on the transmissive display as if it is superimposed and displayed in the real space that is visually recognized through the transmissive display and immediately understand the place where the virus may be attached.

(Variation 2)

The information output unit 181 may display the information indicating the heat trace region on a display so as to be superimposed on an image or a video in a certain range which is the photographing range.

Examples of the display include a digital signage, a smartphone, a tablet terminal, an electric bulletin board, and a TV. For example, the information output unit 181 may display information indicating the heat trace region on a display so as to be superimposed on an actual object image or a visible image. The actual object image or visible image is the actual object image or visible image acquired by the actual object image acquisition unit 110 or the visible image acquisition unit 11. For example, the information output unit 181 may display information indicating the heat trace region on a display so as to be superimposed on an image or video in a certain range, which is a photographing range, taken by a camera different from the visible light camera 21 and the actual object camera 210. An example of a camera different from the visible light camera 21 and the actual object camera 210 is a camera provided in a smartphone or a tablet terminal.

Note that, for example, using AR (Augmented Reality) technology, information indicating the heat trace region may be superimposed on an image or video in a certain range, which is the photographing range. For example, the information output unit 181 detects the position and direction of the display of a smartphone or a tablet terminal to display an image or a video in which the information indicating the heat trace region is superimposed on an image of a video in a certain range on the display so that the actual object existing in the real space (that is, the photographing range of the actual object camera and the thermal camera) visually recognized by the user without the display and the image of the actual object included in the image or the video displayed on the display are aligned. In this case, since the real space visually recognized by the user without the display and the space displayed on the display are aligned in real time according to the position and the angle of the smartphone or the tablet terminal, the user can more immediately understand the place where the virus or the like may be attached.

(Variation 3)

The information output unit 181 may output the information indicating the heat trace region via sound. For example, the information output unit 181 may output a voice such as "X people touched here". For this purpose, the information output unit 181 may store the number of times x the heat trace region was extracted. The information output unit 181 may output a warning sound when the number of times the heat trace region was extracted after disinfection exceeds a predetermined number of times. The warning sound may be voice or non-voice.

The information output unit 181 may change the presence/absence of a warning and/or the warning sound according to the movement of the user.

For example, the information output unit 181 may output a sound expressed in a stronger expression method as the distance between the heat trace region and a person or the hand of the person included in the visible image or the actual object image photographed by the visible light camera 21 or the actual object camera 210 decreases. An example of a sound expressed in a stronger expression method as the distance between the heat trace region and the person or the hand of the person decreases is that the sound is louder as the distance between the heat trace region and the person or the hand of the person decreases. The information output unit 181 may output information indicating the heat trace region via sound only when the distance between the heat trace region and the person or the hand of the person included in the visible image or the actual object image photographed by the visible light camera 21 or the actual object camera 210 is equal to or less than a predetermined distance.

The information output unit 181 may output a sound expressed in a stronger expression method as the distance between the heat trace region and the person or the hand of the person decreases using two or more directional speakers having different sound transmission regions. In this case, the information output unit 181 performs control so that the directional speaker whose distance between the heat trace region and the sound transmission region is shorter outputs the sound expressed in a stronger expression method.

(Variation 4)

The information output unit 181 may display the information indicating the heat trace region via text. For example, the information output unit 181 may send a text corresponding to the information indicating the heat trace region using an e-mail, a short message service, a notification or message function in an Social Network Service (SNS). The text corresponding to the information indicating the heat trace region is transmitted to, for example, a manager of the photographing range and a person who disinfects the photographing range. The destination of the text corresponding to the information indicating the heat trace region may be one or more destinations, or may be two or more destinations.

The information output unit 181 may store the number of times x the heat trace region was extracted, and output a text corresponding to the information indicating the heat trace region when the number of times the heat trace region was extracted exceeds a predetermined number of times. The information output unit 181 may project a text such as "someone touched the door" with a projector or display it on a display. Examples of the display here include a digital signage, an electric bulletin board, and a TV installed near the photographing range.

(Variation 5)

The information output unit 181 may output information indicating a region other than the heat trace region instead of the information indicating the heat trace region. The region other than the heat trace region is a region where the temperature has not risen due to contact with a person, that is, a region where it is unlikely that a virus such as a new coronavirus is attached. By showing a region where it is unlikely that a virus such as a new coronavirus is attached, it is possible to present the user with a region that is safe to touch.

For example, the information output unit 181 may brightly display information indicating a region other than the heat trace region. The information output unit 181 may divide a region other than the heat trace region into a plurality of partial regions, randomly select one of the partial regions, and brightly display information indicating the selected partial region. As a result, the information output unit 181 can present the user with a region that is safe to touch, for example, in the handrail. The information output unit 181 may display information indicating a region other than the heat trace region brighter than the information indicating the heat trace region. For this purpose, for example, the information output unit 181 displays the photographing range brightly in advance, and when the heat trace region is extracted, the extracted heat trace region is darkly displayed.

(Variation 6)

Figure 22:
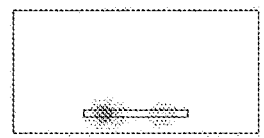
FIG. 22 is a diagram for explaining the fifth embodiment.

The information output unit 181 may display information indicating the heat trace region in a different expression method depending on the number of times the heat trace region was extracted. That is, the information output unit 181 may output different information as information indicating the heat trace region, depending on the number of times the heat trace region was extracted. For example, the information output unit 181 may display a region in a stronger expression method as the number of times the region was extracted as the heat trace region increases. For example, as illustrated in FIG. 22, the information output unit 181 may display a region in a darker color as the number of times the region was extracted as the heat trace region increases. By doing so, it is possible to inform the user that the darker the region, the more it should not be touched or should be disinfected.

Although an embodiment of the present invention has been described in detail above, the present invention is not limited to the specific embodiment described above, and various modified example and changes can be made within the concept of the present invention described in the claims.

The invention claimed is:

1. A device for extracting a heat trace region, the device comprising a processor configured to execute a method comprising:

generating a difference actual object image, wherein the difference actual object image includes a first image based on a difference between a first actual object image and a background actual object image, wherein the first actual object image includes a second image of an actual object obtained by photographing a predetermined range with an actual object camera for photographing the actual object, and the background actual object image includes a second actual object image of a background of the predetermined range;

generating a difference thermal image, wherein the difference thermal image includes a third image based on a difference between a first thermal image and a background thermal image, wherein the first thermal image indicates heat emitted by the actual object obtained by photographing the predetermined range with a thermal camera for photographing the heat emitted by the actual object, and the background thermal image includes a thermal image of the background of the predetermined range; and extracting the heat trace region by removing a region of the actual object from the thermal image based on the difference actual object image and the difference thermal image.

2. The device according to claim 1, the processor further configured to execute a method comprising:
projecting information indicating the extracted heat trace region onto the predetermined range with visible light, wherein
a first wavelength band of electromagnetic waves obtained by the actual object camera and a second wavelength band of electromagnetic waves obtained by the thermal camera do not overlap with a third wavelength band of the projected visible light.

3. The device according to claim 2, wherein
the extracting further comprises extracting, as the heat trace region, a region which is not similar to any of one or more difference actual object regions among one or more difference thermal regions, using each region different from the background thermal image in the difference actual object image as a difference actual object region and using each region different from the background thermal image in the difference thermal image as a difference thermal region.

4. The device according to claim 1, wherein
the extracting further comprises extracting, as the heat trace region, a region which is not similar to any of one or more difference actual object regions among one or more difference thermal regions, using each region different from the background thermal image in the difference actual object image as a difference actual object region and using each region different from the background thermal image in the difference thermal image as a difference thermal region.

5. The device according to claim 1, the processor further configured to execute a method comprising:
causing display of the heat trace region as a region where a person has touched an object appearing within the predetermined range.

6. The device according to claim 1, the processor further configured to execute a method comprising:
causing display of the heat trace region as a region where a person has touched an object appearing within the predetermined range, and wherein the person is infected with a virus.

7. The device according to claim 1, wherein the actual object includes at least a part of a hand of a person.

8. The device according to claim 1, wherein the generating the difference thermal image is further based on a time lapse between the thermal image and the background thermal image.

9. A computer implemented method for extracting a heat trace region, comprising:
generating a difference actual object image, wherein the difference actual object image includes a first image based on a difference between a first actual object image and a background actual object image, wherein the first actual object image includes a second image of an actual object obtained by photographing a predetermined range with an actual object camera for photographing the actual object, and the background actual object image includes a second actual object image of a background of the predetermined range;

generating a difference thermal image, wherein the difference thermal image includes a third image based on a difference between a first thermal image and a background thermal image, wherein the first thermal image indicates heat emitted by the actual object obtained by photographing the predetermined range with a thermal camera for photographing the heat emitted by the actual object, and the background thermal image includes a thermal image of the background; and extracting the heat trace region by removing a region of the actual object from the thermal image based on the difference actual object image and the difference thermal image.

10. The computer implemented method according to claim 9, further comprising:
projecting information indicating the extracted heat trace region onto the predetermined range with visible light, wherein
a first wavelength band of electromagnetic waves obtained by the actual object camera and a second wavelength band of electromagnetic waves obtained by the thermal camera do not overlap with a third wavelength band of the projected visible light.

11. The computer implemented method according to claim 9, further comprising:
projecting information indicating the extracted heat trace region onto the predetermined range with visible light, wherein
a first wavelength band of electromagnetic waves obtained by the actual object camera and a second wavelength band of electromagnetic waves obtained by the thermal camera do not overlap with a third wavelength band of the projected visible light.

12. The computer implemented method according to claim 9, wherein
the extracting further comprises extracting, as the heat trace region, a region which is not similar to any of one or more difference actual object regions among one or more difference thermal regions, using each region different from the background thermal image in the difference actual object image as a difference actual object region and using each region different from the background thermal image in the difference thermal image as a difference thermal region.

13. The computer implemented method according to claim 9, further comprising:
causing display of the heat trace region as a region where a person has touched an object appearing within the predetermined range.

14. The computer implemented method according to claim 9, further comprising:
causing display of the heat trace region as a region where a person has touched an object appearing within the predetermined range, and wherein the person is infected with a virus.

15. The computer implemented method according to claim 9, wherein the actual object includes at least a part of a hand of a person.

16. The computer implemented method according to claim 9, wherein the generating the difference thermal image is further based on a time lapse between the thermal image and the background thermal image.

17. A computer-readable non-transitory recording medium storing computer-executable program instructions that when executed by a processor cause a computer system to execute a method comprising:
   generating a difference actual object image, wherein the difference actual object image includes a first image based on a difference between a first actual object image and a background actual object image, wherein the first actual object image includes a second image of an actual object obtained by photographing a predetermined range with an actual object camera for photographing the actual object, and the background actual object image includes a second actual object image of a background of the predetermined range;
   generating a difference thermal image, wherein the difference thermal image includes a third image based on a difference between a first thermal image and a background thermal image, wherein the first thermal image indicates heat emitted by the actual object obtained by photographing the predetermined range with a thermal camera for photographing the heat emitted by the actual object, and the background thermal image includes a thermal image of the background; and
   extracting a heat trace region by removing a region of the actual object from the thermal image based on the difference actual object image and the difference thermal image.

18. The computer-readable non-transitory recording medium according to claim 17, the computer-executable program instructions when executed further causing the computer system to execute a method comprising:
   projecting information indicating the extracted heat trace region onto the predetermined range with visible light, wherein
      a first wavelength band of electromagnetic waves obtained by the actual object camera and a second wavelength band of electromagnetic waves obtained by the thermal camera do not overlap with a third wavelength band of the projected visible light.

19. The computer-readable non-transitory recording medium according to claim 17, wherein
   the extracting further comprises extracting, as the heat trace region, a region which is not similar to any of one or more difference actual object regions among one or more difference thermal regions, using each region different from the background thermal image in the difference actual object image as a difference actual object region and using each region different from the background thermal image in the difference thermal image as a difference thermal region.

20. The computer-readable non-transitory recording medium according to claim 17, wherein the generating the difference thermal image is further based on a time lapse between the thermal image and the background thermal image, and
   the computer-executable program instructions when executed further causing the computer system to execute a method comprising:
   causing display of the heat trace region as a region where a person has touched an object appearing within the predetermined range, wherein the person is infected with a virus.

\* \* \* \* \*